US007211566B2

(12) United States Patent
Regoli et al.

(10) Patent No.: US 7,211,566 B2
(45) Date of Patent: May 1, 2007

(54) SELECTIVE BRADYKININ (BK) B1 PEPTIDIC RECEPTOR ANTAGONISTS AND USES THEREOF

(75) Inventors: Domenico Regoli, Magog (CA);
Witold Neugebauer, Ottawa (CA);
Fernand Gobeil, Sherbrooke (CA);
Bichov Gabra, Fleurimont (CA);
Pierre Sirois, Orford (CA)

(73) Assignee: Universite De Sherbrooke, Sherbrooke, Quebec (CA)

( * ) Notice: Subject to any disclaimer, the term of this patent is extended or adjusted under 35 U.S.C. 154(b) by 466 days.

(21) Appl. No.: 10/405,088

(22) Filed: Apr. 1, 2003

(65) Prior Publication Data

US 2004/0198666 A1    Oct. 7, 2004

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. .................................. 514/15; 530/328
(58) Field of Classification Search .................... None
See application file for complete search history.

(56) References Cited

U.S. PATENT DOCUMENTS

| | | | |
|---|---|---|---|
| 5,610,140 A | 3/1997 | Goodfellow et al. | |
| 5,635,593 A | 6/1997 | Cheronis et al. | |
| 5,700,779 A | 12/1997 | Goodfellow et al. | |
| 5,750,506 A | 5/1998 | Goodfellow et al. | |
| 5,834,431 A | 11/1998 | Stewart et al. | |
| 5,843,900 A | 12/1998 | Cheronis et al. | |
| 5,849,312 A | 12/1998 | Breton et al. | |
| 5,849,863 A | 12/1998 | Stewart et al. | |
| 5,863,899 A | 1/1999 | Cheronis et al. | |
| 6,015,812 A | 1/2000 | Ferrari et al. | |
| 6,075,120 A | 6/2000 | Cheronis et al. | |
| 6,241,993 B1 | 6/2001 | Breton et al. | |
| 6,468,972 B1 | 10/2002 | Pruche et al. | |
| 2004/0198666 A1* | 10/2004 | Regoli et al. ................. | 514/15 |

FOREIGN PATENT DOCUMENTS

| | | |
|---|---|---|
| WO | WO97/09346 | 3/1997 |
| WO | WO97/25315 | 7/1997 |
| WO | WO98/07746 | 2/1998 |
| WO | WO00/75107 | 12/2000 |
| WO | WO01/05783 | 1/2001 |

OTHER PUBLICATIONS

Bedos, et al., *J. Med. Chem.*, 43: 2387-2394, (2000).
Béliveau, et al., *Clinical Cancer Research*, 8:1242-1250, (2002).
Bhargava and Zhao, *Neuropeptides*, 30:219-223, (1996).
Bhoola et al., *Pharmacol. Rev.*, 44:1-80, (1992).
Chakir and Plante, *Prostagl. Leukot. Essent. Fatty Acids*, 54:45-51, (1996).
Coderre and Rollman, *Life Sci.*, 32:2139-2146, (1983).
D'Amour and Smith, *J. Pharmacol. Exp. Ther.*, 72:74-79, (1941).
Davis et al., *Brazilian J. Med. Bil Res..*, 27:1793-1802, (1994).
Drapeau et al., *J. Pharmacol. Exp. Ther.*, 259:997-1003, (1991).
Drapeau et al., *J. Pharmacol. Exp. Ther.*, 266:192-198, (1993).
Drapeau and Regoli, *Methods in Enzymol*, 163:263-272, (1988).
Dray and Perkins, *Trends Neurosci.*, 16:99-104, (1993).
Eddy and Leimbach, *J. Pharmacol. Exp. Ther.*, 107:385-389, (1953).
Erdös and Skidgel, *Hypertension*, 8:34-37, (1986).
Erdös and Skidgel, "The Kinin System", Academic Press, London, U.K., pp. 111-141, (1997).
Farmer, "The Kinin System", Academic Press, London, U.K., pp. 249-263, (1997).
Ferreira and Vane, *Br. J. Pharmacol.*, 108:124-143, (1967).
Gabra and Sirois, $11^{th}$ National Conference of the Inflammation Research Association, Bolton Landing, NY U.S.A. (Poster and Oral Presentation; Inflamm. Res. Abst., (2002).
Gabra and Sirois, $62^{nd}$ Scientific Sessions of the Am. Diabetes Ass., San Francisco, CA, U.S.A. (Poster Presentation-Late Breaking Abstract), (2002).
Gabra and Sirois, *Eur. J. Pharmacol.*, 457(2-3):115-24, (2002).
Gama Landgraf et al., *Eur. J. Pharmacol.*, 460(1):75-83, (2003).
Gaudreau et al., *Can. J. Physiol Pharmacol.*, 59:371-379, (1981).
Gobeil et al., *Br. J. Pharmacol.*, 118:289-294, (1996).
Gobeil et al., *Can. J. Physiol. Pharmacol.*, 74:137-144, (1996).
Gobeil et al., *Hypertension*, 28:833-839, (1996).
Gobeil et al., *Hypertension*, 33:823-829, (1999).
Hargreaves et al., *Pain*, 32:77-88, (1988).
Hilgenfeldt et al., *Analyt. Biochem.*, 228:35-41, (1995).
Horlick et al., *Immunopharmacol.*, 43:169-177, (1999).
Kung et al., *Int. Arch. Allergy Immunol.*, 105:83-90, (1994).
Larrivée et al., *Br. J. Pharmacol.*, 131:885-892, (2000).
Maggiora et al., *J. Med. Chem.*, 42:2394-2402, (1999).
Marceau et al., *Pharmacol. Rev.*, 50:357-386, (1998).
Marceau, *Immunopharmacol.*, 30:1-26, (1995).
Mason et al., *Can. J. Physiol. Pharmacol.*, 80:264-268, (2002).
McEvoy et al., *J. Clin. Invest.*, 74:715-722, (1984).
Menke et al., *J. Biol. Chem.*, 269:21583-21586, (1994).
Miskolzie et al., *J Biomol. Struc.t Dyn.*, 19:585-593, (2002).
Neugebauer et al., *Can. J. Physiol. Pharmacol.*, 80:287-292, (2002).
Neugebauer et al., *Proceedings of The $27^{th}$ European Peptide*

(Continued)

*Primary Examiner*—Cecilia J Tsang
*Assistant Examiner*—Marcela M Cordero Garcia
(74) *Attorney, Agent, or Firm*—Nixon Peabody LLP

(57) ABSTRACT

The present invention provides for a novel peptidic antagonist for the bradykinin B1 ($BKB_1$) receptor having very good to excellent affinities and selectivity for the $BKB_1$ receptor, in vitro and in vivo increase resistance to enzymatic degradation, superior pharmacokinetic properties, capability to significantly reduce microvascular leakage observed alongside diabetic-induced increase in vascular permeability, capability to significantly reduced the state of hyperalgesia alongside diabetes, capability to significantly reduce the infiltration of pro-inflammatory cells and general state of inflammation alongside allergic asthma.

15 Claims, 14 Drawing Sheets

OTHER PUBLICATIONS

Society Symposium, Sorrento, Italy, (Aug. 31-Sep. 6, 2002).
Ozturk et al., *Curr. Pharma. Des.*, 7:135-161, (2001).
Perron et al., *Eur. J. Pharmacol.*, 376:83-89, (1999).
Plante et al., *Can. J. Physiol Pharmacol.*, 74:824-833, (1996).
Regoli et al., *Can. J. Physiol. Pharmacol.*, 55:855-867, (1977).
Regoli et al., *Eur. J. Pharm.*, 348:1-10, (1998).
Regoli et al., *Embryonic Encyclopedia of Life Sciences*, No. 785998, pp. 1-9, (1999).
Regoli and Barabé, *Pharmacol. Rev.*, 32:1-46, (1980).
Regoli, Park, and Rioux, *Can. J. Physiol. Pharmacol.*, 51:114-121, (1973).
Schild, *Brit. J. Pharmacol.*, 2:189-206, (1947).
Sirois et al., *16th Int. Symposium on Kallikrein-Kinin System*, Charleston, SC, USA (Abst), (2002).
Skidgel and Erdös, *Immunol. Rev.*, 161:129-141, (1998).
Stewart et al., *Can. J. Physiol. Pharmacol.*, 75:719-724, (1997).
Stewart et al., *Can. J. Physiol. Pharmacol.*, 80:275-280, (2002).
Zuccollo et al. *Can. J. Physiol. Pharmacol.*, 74:586-589, (1996).

* cited by examiner

SELECTIVE BRADYKININ (BK) B1 PEPTIDIC RECEPTOR ANTAGONISTS AND USES THEREOF

TECHNICAL FIELD

The present invention relates to Bradykinin B1 ($BKB_1$) receptor antagonists for treating conditions wherein $BKB_1$ receptors are expressed, particularly inflammation, diabetic vasculopathies-related to microvascular leakage, pain, and lung cell infiltration and activation.

BACKGROUND OF THE INVENTION

The kallikreins-kinins system is composed of two major proteolytic systems (in plasma and tissues) that are responsible for the liberation of pro-inflammatory substances, bradykinin (BK) and kallidin (LysBK). Kinins are formed from precursors (high and low molecular weight kininogens, HMWK and LMWK) by the action of serine-proteases named kallikreins. Two types of kallikreins may generate kinins, the first, from hepatic origin, is present in circulating blood and the other is found in many tissues and exocrine glands. Main substrate for plasma kallikrein is the HMWK, the precursor of the nonapeptide BK. Tissue kallikreins originate from many cell types (epithelial and endothelial cells, smooth muscles, blood cells, neurones, etc) and belong to a polygenic family. In vitro, tissue prekallikreins may be converted into active kallikreins by some proteases such as trypsin and plasmin. Tissue kallikreins preferentially cleave the LMWK to generate LysBK. LysBK can be converted to BK by aminopeptidases. BK and LysBK may be further converted by carboxypeptidases of the M type (CPM) and the N type (CPN) into metabolites devoid of the C-terminal arginyl residue (desArg$^9$BK and Lys-desArg$^9$BK) which display distinct biological activities mediated by a receptor type called $BKB_1$ (see below). It has also been shown that activated mast cells, basophils or neutrophils secrete substances with kallikrein-like activities; for instance elastases that enable the formation of kinins (Bhoola et al. 1992, Pharmacol Rev 44, 1–80). Half life of kinins is estimated to be less than 30 sec in human. The short lasting effects of kinins in vivo have been attributed to the rapid degradation of these peptides by proteolytic enzymes circulating in blood or anchored to cell surfaces, especially of the endothelium. Peptidases involved in kinin inactivation are called kininases. The importance of each enzyme in kinin metabolism differ from species to species, from tissue to tissue, and also depends on the conditions (normal vs. inflamed) prevailing in tissues under physiological or pathological states. The most active enzymes that are believed to be involved in kinin degradation are enzyme commission numbers [3.4.11.2]; [3.4.11.9]; [3.4.13.9]; [3.4.13.8]; [3.4.24.11]; [3.4.15.1]; [3.4.24.15]; [3.4.24.16]; [3.4.21.1]; [3.4.17.1]; and [3.4.21.26].

Kinins can be degraded by three categories of enzymes namely the aminopeptidases, the endopeptidases and the carboxypeptidases. Hydrolytic actions of endopeptidases yield inactive fragments. The action of aminopeptidase M (AmM) does not influence the biological activities of bradykinin B2 ($BKB_2$) receptor agonists since BK and LysBK are equally active; however, deletion of N-terminal Lys causes a drastic loss of activity on the human $BKB_1$ receptor because Lys-desArg$^9$BK is 100 fold more potent than desArg$^9$BK (Gobeil et al. 1996, Br J Pharmacol 118, 289–294). Among kininases, the angiotensin converting enzyme (ACE, alias kininase II) and the CPN (Kininase I) have been extensively studied. Both enzymes are zinc-metalloproteases; the former being strongly expressed in lung endothelial cells (and many other tissues); smooth muscles, epithelia and fibroblasts), the latter being confined to the bloodstream. While ACE is responsible for the production of inactive kinin fragments, the plasma CPN and tissue CPM are implicated in the release of active metabolites acting at the $BKB_1$ receptor. Interestingly one of this ectoenzymes, the CPM, can be up regulated (in some experimental pathologies such as endotoxemia), a biological phenomenon that parallels the induction of $BKB_1$ receptors as well as the enhanced formation of $BKB_1$ receptor stimulants in the cardiovascular system and tissue compartments (Erdös and Skidgel, 1997, The kinin system, Academic Press, London UK, pp 111–141).

Receptors for Kinins

The various actions of BK, LysBK and their metabolites are mediated by two receptor subtypes, called $BKB_1$ and $BKB_2$ (Regoli and Barabé, 1980, Pharmacol Rev 32, 1–46). These are rhodopsin-like proteins which coupled to various G proteins that differ from one to another target cell. $BKB_2$ receptor is constitutive and is found in a variety of cells as endothelia, smooth muscles, epithelia, white blood cells: it mediates smooth muscle contraction and the release of autacoids, particularly from the endothelium: this function provides the basic mechanism of peripheral vasodilatation which is responsible for a large part of the in vivo hypotensive effect. Similar to $BKB_1$, the $BKB_2$ receptor has been cloned in human, rabbit, rat and mouse: the $BKB_2$ are small proteins composed of 360–367 amino acids, slightly larger than the $BKB_1$ receptor, because of the presence of a larger C-terminal cytoplasmic segment. The $BKB_2$ receptor has been characterized by mean of selective agonists and antagonists in pharmacological and biochemical assays, using native and recombinant receptors from various species (Regoli et al. 1998, Eur J Pharm 348, 1–10).

The $BKB_1$ receptor is usually not found in physiological conditions but it is induced by various stimuli in several cell types including endothelial, smooth muscle and blood cells, neurons (Marceau et al. 1998, Pharmacol Rev 50, 357–386). $BKB_1$ receptor activation is not as rapid as that of the $BKB_2$ and the effects are more stable and slowly reversible than those of the $BKB_2$ receptor. According to Marceau et al (supra), "the specific role of $BKB_1$ receptor induction may be to amplify the tissue effects of kinins as a function of time via the synthesis of novel receptor molecules that are resistant to tachyphylaxis". $BKB_1$ receptors of human, rabbit, rat and mouse have been cloned and shown to be small proteins of 334–353 amino acids. They mediate contraction of vascular and other smooth muscles as well as the decrease of blood pressure, which in large part is due to peripheral vasodilatation when desArg$^9$BK is applied intravenously in LPS-treated rabbits. $BKB_1$ receptors have been characterized with selective agonists and antagonists, using the classical criteria of the order of potency of agonists and the values of apparent affinities of competitive antagonists.

The Kallikrein-Kinin System in Pathophysiology

The kallikrein-kinin system has been implicated in a variety of physiological functions as well as of pathological states. Indeed, the involvement of kinins has been reported both in the acute and in the chronic phases of inflammation, in pain, in septic inflammatory response syndrome (SIRS), in pancreatitis, in asthma and allergic rhinitis; moreover a protective role of kinins in myocardial ischemia has been suggested (Farmer et al., 1997, The Kinin System, Academic Press, London UK).

In inflammation and pain, tumor, rubor, calor and lesa function are the four cardinal signs of inflammation and exogenous kinin $BKB_1$ and $BKB_2$ receptor agonists can produce all of them when applied to animal and human tissues. Tumor, rubor, calor derive from arterial vasodilatation and the endothelium contraction at the postcapillary veins, while pain is due to activation of receptors in the sensory nerves and the potentiating effect of prostaglandins. Kinin contribute to the acute tissue reaction to noxious stimuli by promoting the release of histamine and, in some species, serotonin from mast cells and that of neuropeptides (e.g. substance P) from sensory nerves: they also contribute to tissue repair by activating cell division, motility and functions of tissue and blood components as macrophages, fibroblasts (e.g. from foetal human lung) and the synthesis of collagen. $BKB_2$ receptors appear to be implicated in the early stage and $BKB_1$ receptors in the late stage of the inflammatory process. Inducible $BKB_1$ receptors are involved in various types of inflammation, diabetic and other types of vasculopathies, pain and angiogenesis (Marceau et al. supra). Recent reports point to an important role of kinin $BKB_1$ receptors in physiopathology. Dray and Perkins (1993, Trends Neurosci 16, 99–104) have reviewed the possible implication of $BKB_1$ receptors in various inflammatory states, tissue reactions to noxious stimuli and hyperalgesia, particularly the chronic phases of these disturbancies. This has been further supported by recent findings from Davis and coworkers (Davis et al. 1994, J Med Biol Res 27, 1793–1802) in inflammatory hyperalgesia in the rat. As pointed out by Marceau (1995, Immunopharmacol 30, 1–26), "it is conceivable that $BKB_1$ receptors can amplify the responses of injured tissues to kinins and, in some cases, take the relay of $BKB_2$ receptors in chronic pathologies".

Peptidic $BKB_1$ receptor antagonists have been developed in the late seventies (Regoli et al. 1977, Can J Physiol Pharmacol 55, 855–867; Regoli and Barabé 1980, J Pharmacol Rev 32, 1–46). Some progress has been made and peptidic compounds have been improved (Gobeil et al., 1996, Hypertension 28, 833–839; Gobeil et al. 1999, Hypertension 33, 823–829; Neugebauer et al. 2002, Can J Physiol Pharmacol 80, 287–292). Other compounds have been discovered, of peptidic and non-peptidic nature. $BKB_1$ receptor antagonists have been disclosed in various published patent documents (WO97/09346, U.S. Pat. Nos. 6,075,120, US5,863,899, US5,849,863, US5,843,900, US5,834,431, US5,750,506, US5,700,779, US5,635,593, US5,610,140, WO97/25315, WO98/07746, WO00/75107, WO01/05783, WO02/, U.S. Pat. Nos. 6,468,972, US6,241,993, US5,849,312) as well as in non-patent documents (Stewart et al., 1997, Can J Physiol Pharmacol 75: 719–724; Larrivée et al., 2000, Brit J Pharmacol 131: 885–892; Mason et al., 2002, Can J Physiol Pharmacol 80: 264–268; Miskolzie et al., 2002, J Biomol Struct Dyn 19: 585–593; Horlick et al., 1999, Immunopharmacol 43: 169–177; Neugebauer et al, 2002, supra; Bedos et al., 2000, J Med Chem 43: 2387–2394)

Despite the antagonists of the prior art, it would still be highly desirable to provide $BKB_1$ receptor antagonists, that are potent, selective and specific for the $BKB_1$ receptor, and resistant to proteolytic degradation with chemical features that favour their absorption and distribution in the body in order to improve potency and duration of action in vivo.

SUMMARY OF THE INVENTION

One aim of the present invention is to provide $BKB_1$ receptor antagonists, that are potent, selective and specific for the $BKB_1$ receptor, and resistant to proteolytic degradation with chemical features that favor their absorption and distribution in the body in order to improve potency and duration of action in vivo.

In accordance with the present invention, there is provided a $BKB_1$ receptor antagonist with high affinity and selectivity for $BKB_1$ receptors that are more resistant to proteolytic degradation. The antagonist can be used as a therapeutic agent for treating conditions wherein a $BKB_1$-receptor mediated response is present.

In accordance with the present invention, there is also provided a pharmaceutical composition comprising the $BKB_1$ antagonist and a pharmaceutically acceptable carrier.

Further in accordance with the present invention, there is provided a method for treating a patient affected by a condition wherein a $BKB_1$-receptor mediated response is building. Such conditions could result from various types of inflammations (Marceau, 1995, Immunopharmacol 30, 1–26) associated with painful syndromes (Marceau et al. 1998, Pharmacol Rev 50, 357–386), diabetes (Zuccollo et al. 1996, Can J Physiol Pharmacol 74, 586–589) and asthma (Perron et al., 1999, Eur J Pharmacol 376, 83–89; Ozturk et al. 2001, Curr Pharma Des 7, 135–161).

Still in accordance with the present invention, there is provided a compound of the formula (I)

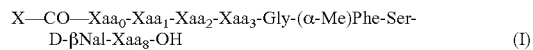

$$X\text{—}CO\text{—}Xaa_0\text{-}Xaa_1\text{-}Xaa_2\text{-}Xaa_3\text{-}Gly\text{-}(\alpha\text{-}Me)Phe\text{-}Ser\text{-}D\text{-}\beta Nal\text{-}Xaa_8\text{-}OH \quad (I)$$

Wherein:

X is $C_nH_{2n+1}$ or $C_iH_{2i}$—$C_6H_5$, where n is an integer from 1 to 3 and i is an integer from 0 to 3;

$Xaa_0$ is Lys, Orn or Cit;

$Xaa_1$ is Arg or Cit, and preferably Arg;

$Xaa_2$ is Oic, Hyp or Pro, and preferably Oic;

$Xaa_3$ is Pro or Oic, and preferably Pro; and $Xaa_8$ is Ile, Leu or Nle, and preferably Ile.

The gene and protein expression of $BKB_1$ receptors are induced during inflammation, pain-related conditions and various other inflammatory diseases and/or disorders such as diabetes and allergic asthma. The present inventors confirm the presence of $BKB_1$ receptors in such various pathological states. $BKB_1$ receptor antagonists are expected to significantly attenuate and/or abolish the symptoms modulated by $BKB_1$ receptors in diabetic (streptozotocin (STZ)-induced) mice such as hyperalgesia and other types of pain, and in allergic asthma (ovalbumin-sensitized) mice as cell infiltration, activation, release of mediators and inflammation.

$BKB_1$ antagonists are therefore useful for treating any condition wherein $BKB_1$ receptors are expressed, particularly inflammation, diabetic vasculopathy-related to microvascular leakage, pain, and lung cell infiltration and activation.

Thus the present invention relates to selective peptidic $BKB_1$ receptor antagonists that at least 1) have an increased affinity and better selectivity, for the $BKB_1$ receptor, thus more potent $BKB_1$ receptor antagonists, 2) are more resistant to in vitro and in vivo enzymatic degradation 3) have superior pharmacokinetic properties, 4) have the capability to significantly reduce microvascular leakage observed alongside which increased vascular permeability in diabetes, 5) have the capability to significantly reduce the state of hyperalgesia alongside diabetes, or 6) have the capability to significantly attenuate the infiltration of pro-inflammatory cells and general state of inflammation alongside allergic asthma.

Accordingly, there is provided a method for treating inflammation, pain and diabetic lesions, said method comprising the step of administering to a patient in need thereof a peptidic $BKB_1$ receptor antagonist compound in accordance with the present invention.

The present invention also provides a method for treating airway and lung inflammation, said method comprising the step of administering to a patient in need thereof a peptidic $BKB_1$ receptor antagonist compound in accordance with the present invention.

The present invention further provides a method for treating asthma comprising the step of administering to a patient in need thereof a peptidic $BKB_1$ receptor antagonist compound in accordance with the present invention.

Still, the present invention provides a method for treating inflammation comprising the step of administering to a patient in need thereof a peptidic $BKB_1$ receptor antagonist compound in accordance with the present invention.

In accordance with the present invention there is also provided a method for treating pain and hyperlagesia comprising the step of administering to a patient in need thereof a peptidic $BKB_1$ receptor antagonist compound in accordance with the present invention.

DETAILED DESCRIPTION OF THE PREFERRED EMBODIMENT

Figure 1:
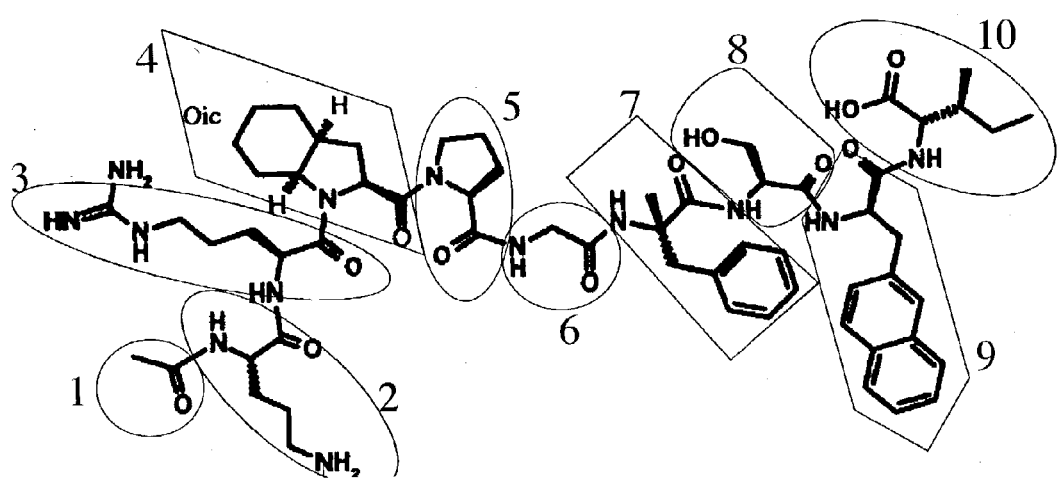
FIG. 1 illustrates the structure of a $BKB_1$ receptor antagonist (compound c) in accordance with one embodiment of the present invention.

The inventors of the present invention have focused on the $BKB_1$ receptor blockade and the therapeutic effects of that blockade. Novel $BKB_1$ receptor antagonists are herein provided. These antagonists are selective to $BKB_1$ receptors, they are resistant to enzymatic degradation and some of them have pharmacokinetic features that promote their absorbance from the skin.

Previous studies with the $BKB_1$ antagonists Lys-[Leu$^8$]desArg$^9$BK showed that this compound completely abolishes the contraction induced by a $BKB_1$ agonist desArg$^9$BK in isolated organs (Regoli and Barabé, 1980, J Pharmacol Rev 32, 1–46) and the changes of blood flow in perfused tissues expressing the $BKB_1$ receptor (Regoli and Barabé, supra) in vivo Lys-[Leu$^8$]desArg$^9$BK has been shown to reduce symptoms of hyperalgesia in STZ diabetic mice, as models of pain. The $BKB_1$ receptor antagonists of the present invention have the same effect on pharmacological assays and in the above described models of animal pathologies.

To facilitate understanding of the design of the new $BKB_1$ receptor antagonists of the present invention, the structures of BK, Lys-BK and their naturally encountered C-terminal truncated fragments are given below:

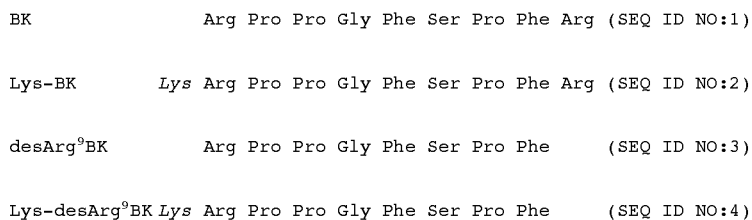

In order to uniformise the nomenclature of the peptides, all substitutions and additions of amino acids (in the N-terminal) are designated as follows: Substitutions are given within brackets by naming substituents and their amino acid position, while additions in the N-terminal precede the opening bracket without numerotation. For example, addition of a N-terminal lysine residue and substitution of a leucine for the phenylalanine at position 8 of desArg$^9$BK is designated Lys-[Leu$^8$]desArg$^9$BK. As far as degradation by proteolytic enzymes is concerned, some details on enzymatic cleavage sites for Lys-desArg$^9$BK are shown in Table 1.

TABLE 1

Enzymatic cleavage sites on Lys-[Leu$^8$]desArg$^9$BK

H-Lys$^0$-Arg$^1$-Pro$^2$-Pro$^3$-Gly$^4$-Phe$^5$-Ser$^6$-Pro$^7$-Leu$^8$-OH

P   1   2   3   4   5   6

| Position of enzyme Activity (P) | Acting enzyme | Enzyme Commission Number |
|---|---|---|
| 1 | Aminopeptidase M | 3.4.11.2 |
| 2 | Aminopeptidase P | 3.4.11.9 |
|   | Prolidase | 3.4.13.9 |
| 3 | Prolinase | 3.4.13.8 |
| 4 | Endopeptidase 24.11 | 3.4.24.11 |
| 5 | Angiotensin converting enzyme | 3.4.15.1 |
|   | Endopeptidase 24.15 | 3.4.24.15 |
|   | Endopeptidase 24.16 | 3.4.24.16 |
|   | Chymotrypsin | 3.4.21.1 |
| 6 | Carboxypeptidase A | 3.4.17.1 |
|   | Prolyl oligopeptidase | 3.4.21.26 |

The present invention thus relates to modifications operated on the peptide-based BKB$_1$ receptor antagonist Lys-[Leu$^8$]desArg$^9$BK (see Table 1) and pharmaceutically acceptable salts thereof. Particular embodiments of the invention relate specifically to substitutions made at strategic positions in the peptide backbone of antagonists in order to withstand enzyme metabolism in the systematic circulation and cerebral and peripheral tissues.

A summary list of enzymes pertaining to the inactivation of classical BKB$_1$ receptor antagonists is presented in Table 1 above. Resistance of BKB$_1$ antagonist analogues to enzymatic degradation can be conveniently assessed by either HPLC analysis following incubation of agent with one of the above listed enzymes or by determining its residual vasodepressor activity after a single passage into the pulmonary circulation in anaesthetised LPS-treated rabbits (Drapeau et al. 1991, J Pharmacol Exp Ther 259, 997–1003; Drapeau et al. 1993, J Pharmacol Exp Ther 266, 192–198; Gobeil et al. 1999, Hypertension 33, 823–829; Neugebauer et al. 2002, Can J Physiol Pharmacol. 80, 287–292).

Following these procedures, alpha-acetylation of N-terminal residue (lysyl, ornityl) at position 0 (P0) proved to be efficient against aminopeptidase M (or N). Substitution of Pro at P2 with non-natural proline surrogate namely Oic, prevented the aminopeptidase P (including prolidase and prolinase) hydrolysis (Neugebauer et al. 2002, Can J Physiol Pharmacol 80, 287–292). Alpha-methylation of Phe at P5 provided a multi-enzymatic resistance toward the activities of endopeptidases 24.11, 24.15 and 24.16, the chymotrypsin and especially the angiotensin converting enzyme (Gobeil et al. 1999, Hypertension 33, 823–829). Finally, replacing Pro at P7 by the highly hydrophobic residue D-β-Nal increased the ligand affinity (antagonist potency) at the human BKB$_1$ receptor (Gobeil et al., supra) and conferred additional enzyme resistance against carboxypeptidase A and prolyl oligopeptidase. Therapeutical efficiency of these newly described highly potent and stable BKB$_1$ antagonists should be good. These chemical changes applied collectively greatly enhanced the in vivo stability (duration of action) and ligand affinity (specificity) of the initially described antagonists (Gobeil et al. 1999, Hypertension 33, 823–829; Neugebauer et al. 2002, Can J Physiol Pharmacol 80, 287–292).

Peptidic BKB$_1$ Receptor Antagonist Synthesis

All peptides were synthesized with an Applied Biosystems 430, a peptide synthesizer using Merrifield type resins with the first amino acid attached. Amino acids were activated by dicyclohexylcarbodiimide/1-hydroxybenzotriazole (Peptides International, Louisville, Ky.) in 1-methyl-2 pyrrolidinone. Peptides were cleaved from the resins with anhydrous HF in the presence of appropriate scavengers. The resulting peptides were purified by medium pressure reversed-phase (C$_{18}$) chromatography and if necessary by HPLC. Peptide purity was assessed by analytical HPLC and identity confirmed by ion-spray mass spectrometry (VG Quattro, Manchester, UK).

First and second generation of BKB$_1$ receptor antagonists are listed below have been described in the prior art:
a) Lys-[Leu$^8$] desArg$^9$BK; and
b) Ac-Lys-[D-βNal$^7$, Ile$^8$] desArg$^9$BK.

There are now provided an advanced generation of BKB$_1$ receptor antagonists as listed below, as compound:
c) Ac-Orn[Oic$^2$,(α-Me)Phe$^5$,D-βNal$^7$,Ile$^8$]desArg$^9$BK (see FIG. 1 for structure);
d) Ac-Lys[Oic$^2$,(α-Me)Phe$^5$,D-βNal$^7$,Ile$^8$]desArg$^9$BK;
e) Ac-Orn[Oic$^2$,Oic$^3$(α-Me)Phe$^5$,D-βNal$^7$,Ile$^8$]desArg$^9$BK;
f) Ac-Lys[Oic$^2$,Oic$^3$(α-Me)Phe$^5$,D-βNal$^7$,Ile$^8$]desArg$^9$BK;
g) Propanoyl-Orn[Oic$^2$,(α-Me)Phe$^5$, D-βNal$^7$,Ile$^8$]desArg$^9$BK
h) Propanoyl-Lys[Oic$^2$,(α-Me)Phe$^5$,D-βNal$^7$,Ile$^8$]desArg$^9$BK;
i) Propanoyl-Orn[Oic$^2$,Oic$^3$(α-Me)Phe$^5$,D-βNal$^7$,Ile$^8$]desArg$^9$BK;
j) Propanoyl-Lys[Oic$^2$,Oic$^3$(α-Me)Phe$^5$,D-βNal$^7$,Ile$^8$]desArg$^9$BK;
k) Butanoyl-Orn[Oic$^2$,(α-Me)Phe$^5$,D-βNal$^7$,Ile$^8$]desArg$^9$BK
l) Butanoyl-Lys[Oic$^2$,(α-Me)Phe$^5$,D-βNal$^7$,Ile$^8$]desArg$^9$BK;
m) Butanoyl-Orn[Oic$^2$,Oic$^3$(α-Me)Phe$^5$,D-βNal$^7$,Ile$^8$]desArg$^9$BK;
n) Butanoyl-Lys[Oic$^2$,Oic$^3$(α-Me)Phe$^5$,D-βNal$^7$,Ile$^8$]desArg$^9$BK;
o) Bz-Orn[Oic$^2$,(α-Me)Phe$^5$,D-βNal$^7$,Ile$^8$]desArg$^9$BK
p) Bz-Lys[Oic$^2$,(α-Me)Phe$^5$,D-βNal$^7$,Ile$^8$]desArg$^9$BK;
q) Bz-Orn[Oic$^2$,Oic$^3$(α-Me)Phe$^5$,D-βNal$^7$,Ile$^8$]desArg$^9$BK;
r) Bz-Lys[Oic$^2$,Oic$^3$(α-Me)Phe$^5$, D-βNal$^7$,Ile$^8$]desArg$^9$BK;
s) 2-phenyl-acetyl-Orn[Oic$^2$,(α-Me)Phe$^5$,D-βNal$^7$,Ile$^8$]desArg$^9$BK
t) 2-phenyl-acetyl-Lys[Oic$^2$,(α-Me)Phe$^5$,D-βNal$^7$,Ile$^8$]desArg$^9$BK;
u) 2-phenyl-acetyl-Orn[Oic$^2$,Oic$^3$(α-Me)Phe$^5$,D-βNal$^7$,Ile$^8$]desArg$^9$BK;
v) 2-phenyl-acetyl-Lys[Oic$^2$,Oic$^3$(α-Me)Phe$^5$,D-βNal$^7$,Ile$^8$]desArg$^9$BK;
w) 3-phenyl-propanoyl-Orn[Oic$^2$,(α-Me)Phe$^5$,D-βNal$^7$,Ile$^8$]desArg$^9$BK
x) 3-phenyl-propanoyl-Lys[Oic$^2$,(α-Me)Phe$^5$,D-βNal$^7$,Ile$^8$]desArg$^9$BK;
y) 3-phenyl-propanoyl-Orn[Oic$^2$,Oic$^3$(α-Me)Phe$^5$,D-βNal$^7$,Ile$^8$]desArg$^9$BK;
z) 3-phenyl-propanoyl-Lys[Oic$^2$,Oic$^3$(α-Me)Phe$^5$,D-βNal$^7$,Ile$^8$]desArg$^9$BK;
aa) 4-phenyl-butanoyl-Orn[Oic$^2$,(α-Me)Phe$^5$,D-βNal$^7$,Ile$^8$]desArg$^9$BK;
bb) 4-phenyl-butanoyl-Lys[Oic$^2$,(α-Me)Phe$^5$,D-βNal$^7$,Ile$^8$]desArg$^9$BK;
cc) 4-phenyl-butanoyl-Orn[Oic$^2$,Oic$^3$(α-Me)Phe$^5$,D-βNal$^7$,Ile$^8$]desArg$^9$BK; and dd) 4-phenyl-butanoyl-Lys[Oic$^2$,Oic$^3$($\alpha$-Me)Phe$^5$,D-$\beta$Nal$^7$, Ile$^8$]desArg$^9$BK.

N-acylation of peptides was performed on the solid phase with acetyl anhydrides or other acyl chlorides.

Effectiveness for one of those novel antagonists in inflammatory diseases such as diabetes (pain, nociception, hyperalgesia, vasculopathy (vascular permeability)) and asthma is demonstrated hereinafter.

In Vitro Bioassays to Assess the Selectivity to BKB$_1$ Receptor Subtype (Isolated Preparations in Organ Baths)

Selected antagonists were tested for activities in three isolated organs: (1) the rabbit aorta (rbA), (2) the human umbilical vein (hUV) and (3) the rabbit jugular vein (rbJV).

All details regarding the procurements of human umbilical cords and rabbit vessels as well as, the procedures for preparing the isolated organs and the experimental protocols are described in these respective publications: rbA (Rioux et al. 1973, Can J Physiol Pharmacol 51, 114–121); hUV (Gobeil et al. 1996, Br J Pharmacol 118, 289–294), and rbJV (Gaudreau et al. 1981, Can J Physiol Pharmacol 59, 371–379).

The rabbit aorta without endothelium (which contains only the BKB$_1$ receptor) was used to determine the antagonistic activities of each compound.

In human, the hUV that contains BKB$_1$ and BKB$_2$ receptors was treated with HOE 140, the BKB$_2$ receptor antagonist, to eliminate the interference of the BKB$_2$ receptor in experiments intended to measure the antagonistic activity of each compound in BKB$_1$ receptor challenged with Lys-desArg$^9$BK.

The rabbit jugular vein (a pure BKB$_2$ receptor system) was used to exclude any action of the new compounds on the BKB$_2$ receptor and thus establish their selectivity. All tissues were treated with captopril (1 $\mu$M) to prevent the degradation of the peptidic agonists.

Repeated applications of a single and double concentration of BK (on rbJV,) or of desArg$^9$BK (rbA and hUV) were made in the absence and in presence of the various peptides to evaluate their apparent affinities as antagonists, in terms of pA$_2$ (-log$_{10}$ of the molar concentration of antagonist that reduces the effect of a double concentration of agonist to that of a single one) (Schild 1947, Br J Pharmacol 2, 189–206). The antagonists were applied 10 min before measuring the myotropic effects of either BK (the BKB$_2$ receptor agonist) or Lys-desArg$^9$BK (the BKB$_1$ receptor agonist). All kinin antagonists were initially applied to tissues at concentration of 10 $\mu$g/mL to measure their "potential agonistic activities, ($\alpha^E$)" in comparison with BK (in the BKB$_2$ receptor preparation) or Lys-desArg$^9$BK (in the BKB$_1$ receptor preparations).

The presence of a Lys at the N-terminal is important for the BKB$_1$ receptor antagonist since the affinity of Lys-[Leu$^8$] desArg$^9$BK is higher than that of [Leu$^8$]desArg$^9$BK by at least 1.5 log units which is in agreement with the results of Menke et al. (Menke et al. 1994, J Biol Chem, 269, 21583–21586) who have cloned and characterized the human BKB$_1$ receptor. Replacement of Lys at this position by non-protein amino acid Orn does not change activity level but still can increase enzymatic resistance. A significant gain of affinity for the BKB$_1$ receptor is observed when position 8 is occupied by Ile. The stereospecificity of the residue $\beta$Nal in position 7 is again crucial, likewise in the rabbit, since the isomeric form L-$\beta$al shows 3 orders of magnitude less antagonistic activity than the D-$\beta$Nal form (see Table 2).

TABLE 2

Antagonist potencies (pA$_2$) measured in kinin receptor bioassay systems

| Antagonists | BKB$_1$-R rbA | BKB$_1$-R hUV | BKB$_2$-R rbJV |
|---|---|---|---|
| Lys-[Leu$^8$]desArg$^9$-BK | 8.27 ± 0.13 | 8.01 ± 0.03 | <6.00 |
| Ac-Lys-[D-$\beta$Nal$^7$, Ile$^8$]desArg$^9$-BK | 8.40 ± 0.12 | 8.49 ± 0.10 | <6.00 |
| Ac-Orn-[Oic$^2$, ($\alpha$-Me)Phe$^5$, D-$\beta$Nal$^7$, Ile$^8$] desArg$^9$-BK | 8.64 ± 0.08 | 8.46 ± 0.08 | <6.00 |
| Ac-Lys-[Oic$^2$, ($\alpha$-Me)Phe$^5$, D-$\beta$Nal$^7$, Ile$^8$] desArg$^9$-BK | 8.50 ± 0.10 | 8.43 ± 0.06 | <6.00 |
| Ac-Orn-[Oic$^2$, Oic$^3$, ($\alpha$-Me)Phe$^5$, D-$\beta$Nal$^7$, Ile$^8$] desArg$^9$-BK | 8.30 ± 0.08 | Nd | <6.00 |

Note:
Data are means ± SEM of 4–7 experiments.

In Vitro Biochemical Stability Assays Against Purified Native Enzymes

These assays were performed using three enzyme preparations: purified angiotensin converting enzyme (ACE; from rabbit lung), human plasma as a, source of aminopeptidase M (AmM) and human platelets as a source of aminopeptidase P (AmP).

Rabbit ACE

Purified ACE from rabbit lungs (Sigma, St. Louis, Mo.) was dissolved in PBS (50 mM, pH 7.5, containing 300 mM NaCl and 10 $\mu$M ZnCl$_2$; the final concentration of ACE was 45 $\mu$g/ml). Each of the peptide antagonists (200 $\mu$M) was incubated for 60 min at 37° C. with ACE (8.5 $\mu$l) (total volume medium, 187.5 $\mu$l). The enzymatic reaction was then terminated by boiling. Control experiments showed a proteolytic pattern of Lys-[Leu$^8$]desArg$^9$BK (H-Lys$^o$-Phe$^5$-OH and H-Ser$^6$-Leu$^8$-OH fragments), which is in agreement with that reported for desArg$^9$BK (Skidgel and Erdös, supra); ACE activity could totally be inhibited by captopril (1 $\mu$M) (n=3) (Gobeil et al., 1996, Can J Physiol Pharmacol 74, 137–144).

Human Plasma (AmM)

Human plasma AmM was prepared as previously described (Gobeil et al., 1999, Hypertension, 33, 823–829). Blood (5 ml) was withdrawn from healthy normotensive male Caucasian volunteers and put into heparinized tube (200 U). Blood samples were centrifuged at 1500 rpm for 15 min in a refrigerated tabletop centrifuge. The peptide antagonists (200 $\mu$M) were placed in a PBS buffer (50 mM, pH 7.5, containing 300 mM NaCl) and incubated for 60 min with 50 $\mu$l of human plasma (total volume of the medium, 375 $\mu$l). Immersing samples into boiling water and then cooling them on ice stopped the hydrolysis reaction. Control experiments have shown that ≈70% of the kininase activity that is present in the human plasma is abolished by amastatin (1 $\mu$M) and that the incubation of Lys-[Leu$^8$]desArg$^9$BK with this enzymatic preparation led to the production of [Leu$^8$]desArg$^9$BK as detected by electrospray mass spectrometry.

The experimental protocol for the measurement of ACE activity has been described elsewhere (Drapeau et a). 1993, J Pharmacol Exp Ther 266, 192–198; Gobeil et al., 1996, supra).

Human Platelets (AmP)

Human platelet AmP was prepared as described by Maggiora et al. (1999, J Med Chem 42, 2394–2402). Human platelets (40 ml) were centrifuged at 250×g for 7 min at room temperature. The resulting supernatant was recentrifuged at 2790×g for 15 min at room temperature. Pellets were collected, resuspended in 40 ml of phosphate-buffered saline (PBS) containing 3.5% of sodium citrate, and then re-centrifuged at 2790×g for 15 min at room temperature. This washing step was repeated. Pellets were resuspended in 4 ml of PBS-sodium citrate, snap-frozen in liquid nitrogen, thawed at 37° C., sonicated briefly, and then centrifuged at 43 000×g for 2 h at 4° C. (Sorvall RC 5B, ss-34 rotor). The resulting supernatant was used for enzyme assays as described in Neugebauer et al. (Neugebauer et al. 2002, supra).

Human and animal kallidins have a Lys residue at the N-terminal end, which may probably be the most abundant naturally-occurring kinin analogues present in human plasma and urine. Furthermore, LysBK and Lys-desArg$^9$BK are sensitive to aminopeptidases (e.g. aminopeptidase M: EC 3.4.11.2) and can be protected by N-acetylation. All sensitive positions to enzymatic degradation have been investigated. Because of the predominant role played by ACE, the endothelial enzyme of the pulmonary circulation in the inactivation of both the kinins and their desArg$^9$-metabolites, BKB$_1$ receptor antagonists must be protected if one wishes to prolong their in vivo activities. The fundamental role of a D-residue in position 7 for BKB$_1$ receptor antagonism is supported by the D-βNal replacement. The presence of a D-βNal in position 7 not only protects (quite efficiently) from degradation by ACE, but confers higher affinity (by three log units) and selectivity for the rabbit and human BKB$_1$ receptors. Several substitutions were made at the Phe 8 with Leu, Ile or Ala with the results of lie being the most favorable residue for BKB$_1$ receptor antagonism. The presence of Ala in position 8 suppresses the antagonistic activity, suggesting that a hydrophobic bulky residue is needed in position 8 for BKB$_1$ receptor antagonism.

The insertion at the C-terminal end of enzymatically protecting residues such as D-βNal in position 7 gave rise to more resistant and still selective BKB$_1$ receptor antagonists. The next very sensitive position of the peptide sequence is Phe in position 5, where ACE activity degrades active peptides quite rapidly. Of several changes made in this position, the best result in biological activities and the highest metabolic stabilities were obtained with alpha-methyl L-phenylalanine [(α-Me)Phe]. This metabolic resistance was additional to the change made in position 7. The final metabolic weakness of improved antagonist was position 2, where prolidase activity might cleave active peptides. In the native sequence, the double proline (in 2 and 3 positions) points to the importance of the peptides conformation. Thus any change in the sequence made in this region should conserve the general shape of the original molecule. For this reason non-natural amino acid, which could mimic Pro, would be a good candidate for substitution. There, Oic (octahydro indanyl carboxylic acid) was tested with very good results in antagonistic activity and resistance to enzymatic degradation. N-alpha-acylation of peptide would in some degree protect molecule from amino terminal enzymatic activity.

In summary, several peptides related to desArg$^9$BK were tested as agonists of BKB$_1$ (rabbit aorta, human umbilical vein) and of BKB$_2$ (rabbit jugular vein, guinea pig ileum, human umbilical vein) receptors. The compounds were also incubated with purified ACE from rabbit lung to test their resistance to degradation. Apparent affinities (in terms of pA$_2$) of compounds and their potential residual agonistic activities (α$^E$) were evaluated. Bradykinin and desArg$^9$BK were used as agonists for the BKB$_2$ or the BKB$_1$ receptors, respectively.

The present analysis concerns series of peptides aimed at improving BKB$_1$ receptor antagonism toward obtaining compounds of highed affinity, better selectivity for the BKB$_1$ receptor and greater resistance to degradation by peptidases. To these goals, significant substitutions were made in several positions 0, 2, 5, 7 and 8 of [Leu$^8$]des Arg$^9$BK and acyl residues were added to the N-terminal end (see table 3).

TABLE 3

In vitro metabolic stabilities of BKB$_1$ receptor antagonists against several peptidases.

| Antagonists | Peptide metabolism (%) | | |
|---|---|---|---|
| | Human plasma AmM | Rabbit lung ACE | Human platelets AmP |
| Lys-[Leu$^8$]desArg$^9$BK | 100 | 93 ± 3 | 99 ± 1 |
| Ac-Orn-[Oic$^2$, (α-Me)Phe$^5$, D-βNal$^7$, Ile$^8$]desArg$^9$BK | 0 | 0 | 12 ± 2 |
| Ac-Lys-[Oic$^2$, (α-Me)Phe$^5$, D-βNal$^7$, Ile$^8$]desArg$^9$BK | 0 | 0 | 12 ± 4 |

Note:
Data are means ± SEM of 3 experiments.

Ex vivo and In vivo Pharmacokinetics, and HPLC Analysis of Peptide Digests: Stability of the Drugs Blood Collection in Rats Rats were anesthetized with the administration of ketamine/xylazine (100 mg/ml:0.1 ml/100 g, i.p.). For ex vivo analysis, blood was collected by cardiac puncture and placed into 5 ml vacutainer tubes containing 0.5 ml of 0.1 M Na$_2$CO$_3$ (for blood and plasma). For in vivo analysis, the drug was administered by i.v. bolus (2.5 mg/kg body weight) in the jugular vein of anesthetized rats and blood was collected as described above after 2, 5, 15, 30, 60, 120, 180 and 240 min.

Sample Preparation for Ex vivo Analysis

Blood samples were centrifuged at 300 g and the supernatant (plasma) was collected. To prepare the serum, the blood was transferred to microfuge tubes and left to clot for 1 hour at room temperature. The tubes were then centrifuged at 13 000 rpm for 10 min at 4° C. in a microfuge and the supernatant was collected. Serum and plasma were then filtered through a 0.45 µM filter.

Liver, lung and kidneys were collected from Wistar rats and resuspended in nine volume of PBS. The tissues were homogenized for 3×15 sec. on ice with a Polytron homogenizer and were centrifuged at 3000 rpm for 15 min. at 4° C. The supernatant was collected and kept at −80° C. until used.

Stability studies were initiated by adding the peptide (20–100 µM) to 50–100 µl of either plasma, serum or extract (10–100 µM final concentration) and incubated for 10 min to 24 hours at 37° C. The reaction was stopped by the addition of ice-cold acetonitrile (75% final concentration) containing 10 µM Lys-desArg$^9$BK (which serves as an internal control). The samples were vortexed and centrifuged at 13000 rpm for 20 min at 4° C. in a microfuge. The clear supernatant was transferred to a 1 ml tube and the samples were evaporated to dryness by lyophilisation. Finally, the samples were resuspended in 50 µl of HPLC-grade water.

HPLC Analysis

Quantitative analysis of the extracted compound and standard controls was carried out using an Agilent reverse-phase HPLC (model 1100) coupled to a 4.6×150 mm Zorbax 300SB-C18 column (5 μm particle size) and equipped with a diode array detector. The peptides were eluted at a flow rate of 0.7 ml/min. with a linear gradient ranging from 5 to 65% of acetonitrile/TFA 0.05%/water over 32 min. at 25° C. The elution positions and quantification of compounds were determined by following the absorbance at 226 nm.

Concentrations of the peak's products were estimated using a computer software program (Chemstation for LC 3D, Agilent) that controlled all the chromatography operations.

Figures 2A, 2B:
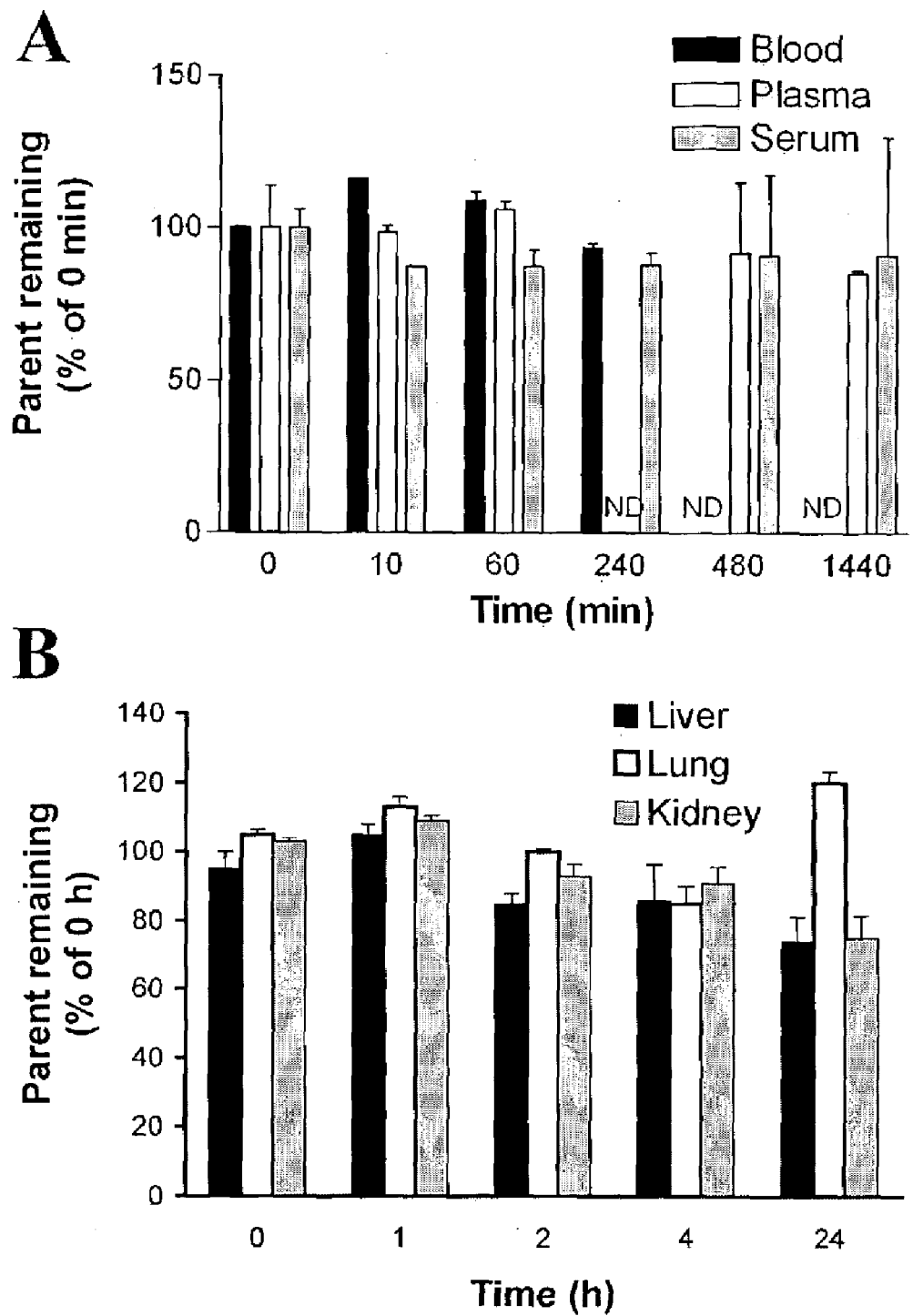
FIGS. 2A and 2B illustrate the stability of one $BKB_1$ antagonist (compound c) in accordance with the present invention over time in various rat biological fluids (FIG. 2A) and tissue extracts (FIG. 2B)
Figure 3:
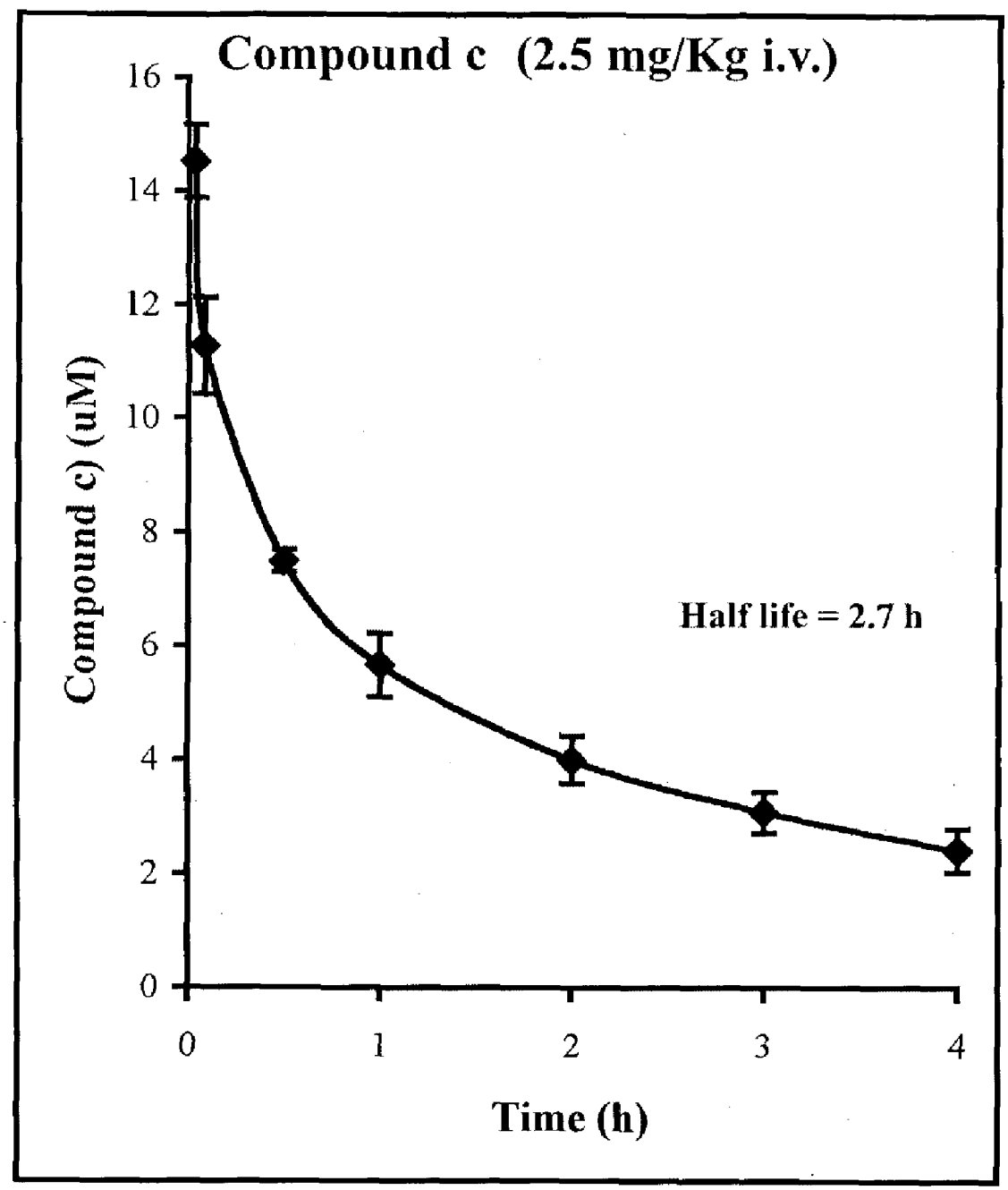
FIG. 3 illustrates the circulatory half-life of the antagonist tested in FIGS. 2A and 2B in rat plasma following bolus i.v. administration.

The antagonists of the present invention are stable in either blood, plasma or serum fluids with >90% parent remaining after 4 hours when tested ex vivo (FIG. 2A). In addition, incubation of the compound c with tissue extracts from liver, lung, and kidney show >75% parent remaining after 24 hours (FIG. 2B). In FIGS. 2A and 2B, ND means not determined;

Compound c possesses a circulatory half-life over 2 hours after direct i.v. jugular administration in anaesthetized rats (FIG. 3).

In Vivo Assay of Type-1 Diabetic Hyperalgesia (in Mice)

Male CD-1 mice weighting between 25–30 g (Charles River Breeding Laboratory, St-Constant, QC, Canada) were used. The mice were housed four by cage with free access to food and water. They were maintained under conditions of standard lighting, (alternating 12-h light/dark cycle), temperature (22±0.5° C.) and humidity (60±10%) with food and water available at libitum. Animals were used only once in a given experiment. Experiments were conducted between 10:00 and 18:00 h.

Streptozotocin (Pharmacia & Upjohn Incorporation, Mississauga, ON, Canada) was dissolved in saline at a pH of 4.5 and administered to mice i.p. The $BKB_1$ agonist desArg$^9$BK and compound c were dissolved in saline and administered to mice i.p.

Insulin-dependent diabetes mellitus (IDDM) was induced in mice using STZ. Male CD-1 mice were given a single high i.p. dose of STZ (200 mg/kg) (McEvoy et al., 1984, J Clin Invest 74, 715–722). The induction of type 1 diabetes was confirmed by measuring the blood glucose level 96 h after STZ administration (Chakir and Plante, 1996, Prostagl Leukot Essent Fatty Acids 54, 45–51). Blood was withdrawn from the retro-orbital sinus of mice with a 50 μl heparinized capillary tube. Blood glucose levels were determined with an automatic analyzer (Glucometer Elite XL, Bayer Incorporation, Toronto, Ontario, Canada) using glucose oxidase/ potassium ferricyanide reagent strips. The diabetic animals used in our study had a blood glucose level higher than 20 mmol/l while the normal value ranged between 5 to 8 mmol/l (Plante et al., 1996, Can J Physiol Pharmacol 74, 824–833). The rate of induction of diabetes was 86%.

STZ-Induced Hyperalgesia

Figure 4:
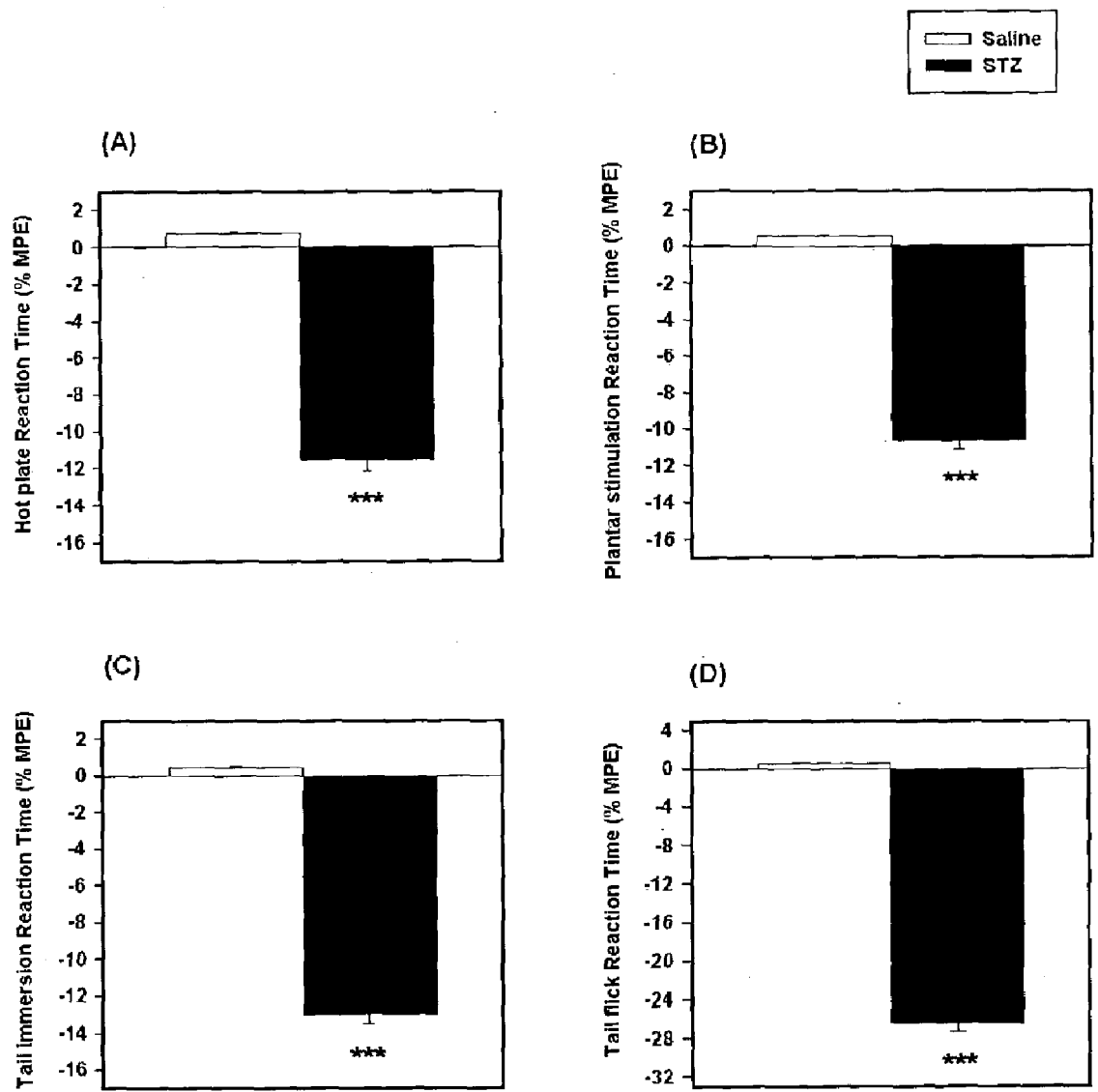
FIGS. 4A to 4D illustrate the evaluation of the nociceptive activity in STZ diabetic mice using the hot plate (FIG. 4A), the plantar stimulation (FIG. 4B), the tail immersion (FIG. 4C) and the tail flick (FIG. 4D) tests.

Mice treated with STZ (200 mg/kg, i.p.) developed a well-defined hyperalgesia, seven days following the induction of diabetes. In the hot plate and plantar stimulation tests (supra-spinal nociceptive tests), the maximum percent effect (MPE) in STZ-diabetic mice was −11.51±0.67 and −10.66±0.42%, respectively compared to 0.76±0.09 and 0.56±0.11% in control mice (FIGS. 4A, 4B). Likewise, in the tail immersion and tail flick tests (spinal nociceptive tests), the MPE was −12.98±0.50 and −26.41±0.90%, respectively in STZ-treated mice versus 0.47±0.05 and 0.53±0.08%, in control non-diabetic mice (FIGS. 4C, 4D). In FIGS. 4A to D, data are expressed as mean % MPE±SEM (n=10–14); n=number of animals; *** significantly different from the saline group at P<0.001.

Nociception was evaluated in both healthy and diabetic mice using four different thermal nociceptive tests as detailed hereinafter.

Hot Plate Test

The hot plate test was adapted from the technique of Eddy and Leimbach (1953, J Pharmacol Exp Ther 107, 385–389). In brief, a plexiglass cylinder (20×14 cm) is used to confine the mouse to the anodized heated surface (275×263 mm) of the apparatus (IITC Hot Plate Analgesia Meter, Life Science, Calif., USA). The plate is adjusted to a temperature of 55° C.±0.5° C. When the pain threshold is reached the animal starts to react by licking its hind paw or to jump, and the reaction time is recorded with a built-in timer, with a maximum cut-off time of 30 s to avoid tissue damage. Mice with latency value between 10–15 s were selected.

Administration (i.p.) of increasing doses of compound c (50–600 μg/kg) did not affect the nociceptive threshold (baseline) in control healthy mice.

Figure 5A:
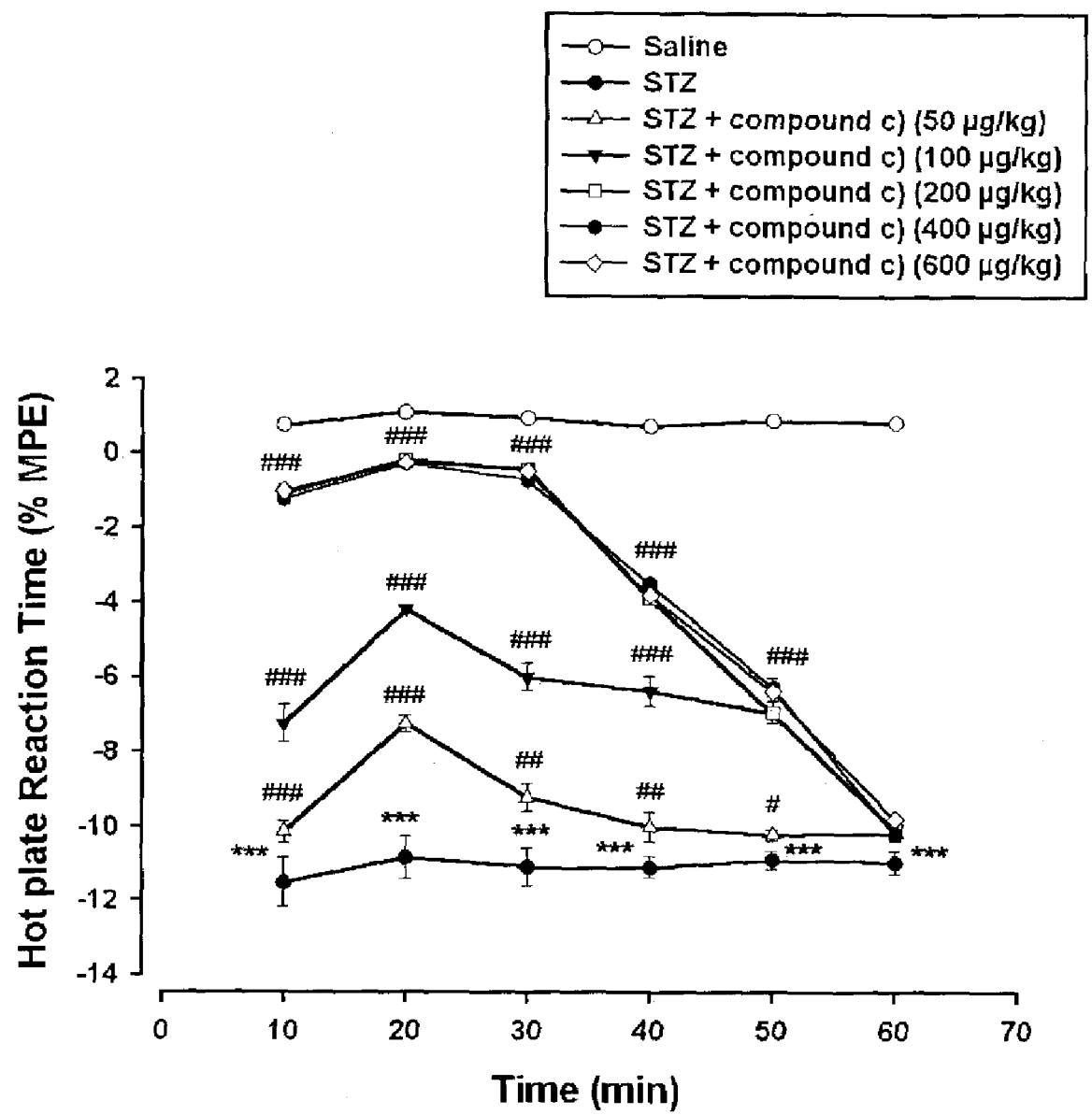
FIGS. 5A and 5B illustrate the effect of acute i.p. administration of the antagonist tested in FIGS. 2A and 2B on nociception in STZ diabetic mice in the hot plate test (FIG. 5A) and in the plantar stimulation test (FIG. 5B) as supraspinal pain tests.

Conversely, compound c administered as described hereinabove, produced a marked inhibition of the hyperalgesic activity observed in diabetic mice, which was dose- and time-dependent. Maximal inhibition was observed after 20 min with all doses of compound c. At a dose of 200 μg/kg, compound c abolished STZ-mediated hyperalgesia (FIG. 5A). Lower dosages (50, 100 μg/kg) still significantly (P<0.0001) inhibited the hyperalgesic activity by 33 and 61%, respectively, after 20 min (maximal inhibition), its effectiveness slowly decreasing but over a period of time up to 50 min. With higher doses (>200 μg/kg), the compound c inhibitory potency was reduced by half at 45 min and completely receded after 60 min (FIG. 5A). Lower doses followed a similar course. The $ID_{50}$ of compound c at the time of the maximal inhibition (20 min) was estimated at 78±3 μg/kg.

Figure 7A:
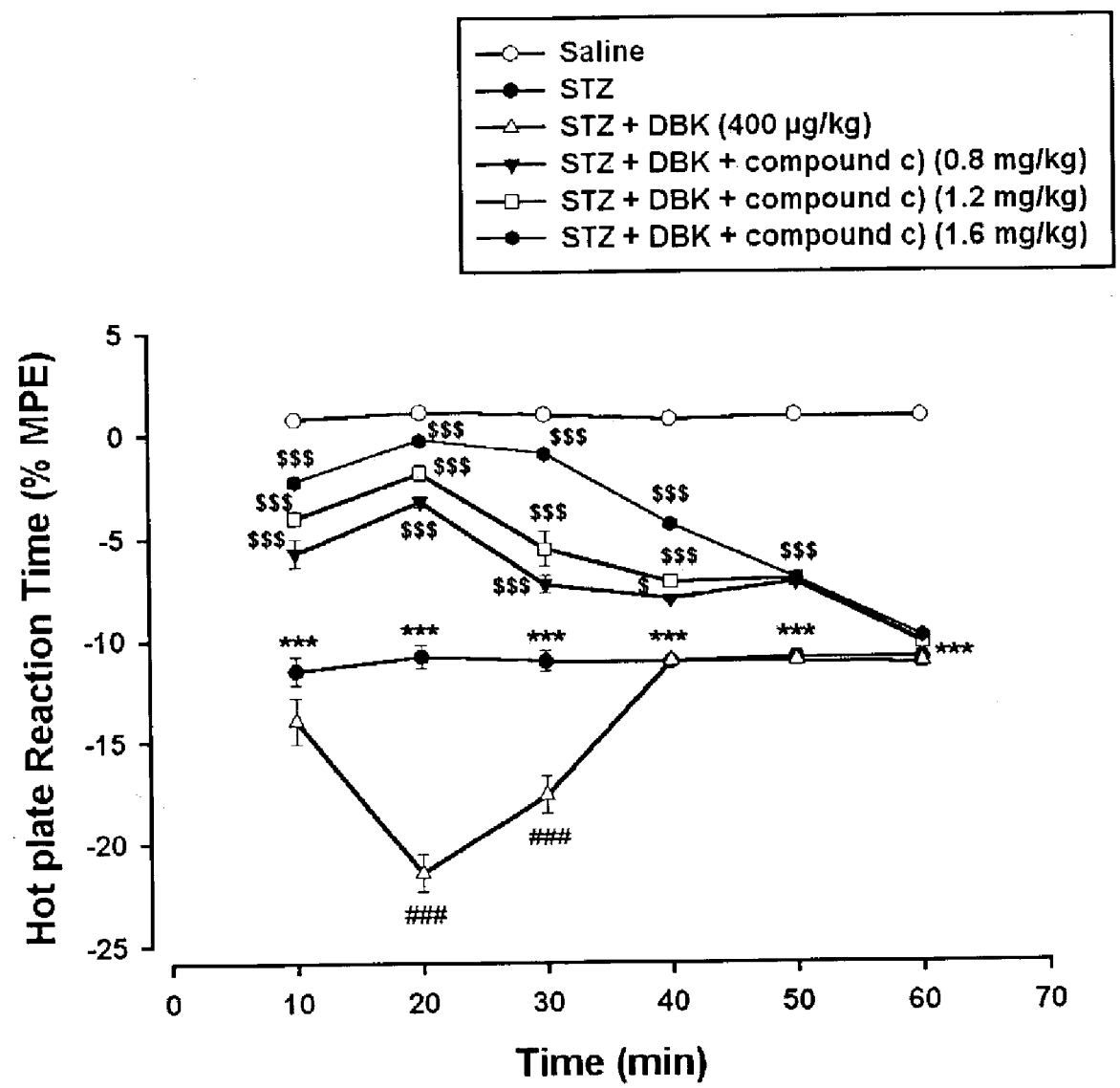
FIGS. 7A and 7B illustrate the effect of acute i.p. combined administration of desArg$^9$BK with the antagonist tested in FIGS. 2A and 2B on nociception in STZ diabetic mice in the hot plate (FIG. 7A) and the plantar stimulation (FIG. 7B) tests.

The selective $BKB_1$ receptor agonist desArg$^9$BK (400 μg/kg i.p.), was exogenously administered to both groups of mice. In control mice, desArg$^9$BK did not induce significant changes in nociceptive response. However, desArg$^9$BK potentiated (P<0.0001; FIG. 7A) the hyperalgesic response by 98% in STZ diabetic mice.

Co-administration of desArg$^9$BK and compound c at selected doses of 1.6, 2.0 and 2.4 mg/kg i.p., reversed the potentiating effect of desArg$^9$BK on diabetic hyperalgesia and produced a marked shift (P<0.0001) in the hot plate latencies to values equivalent to those recorded in the control healthy mice (FIG. 7A).

Plantar Stimulation Test

In the plantar stimulation test, the method of Hargreaves et al. (Hargreaves et al., 1988, Pain, 32, 77–88) was used to access the hind-paw nociceptive withdrawal thresholds of a free moving mouse to thermal stimuli. Mice are placed individually and trained in a plexiglass enclosures on top of a non-heated glass panel (Model IITC 336 Paw/Tail Stimulator Analgesia Meter, Life Science, Calif., USA) and left to acclimatize for 10 min daily for two days before starting the experiments. Light from a halogen bulb lamp (150 W) was delivered to the plantar surface of one of the mouse hind-paws through the base of the glass panel and was focused using an aluminized parabolic mirror mounted on the light source. The time taken for the mouse to lift or lick its hind paw was noted. The intensity of the radiant heat is selected in order to reach a basal latency of 8–10 seconds, and to reduce the variability. A cut-off time of 30 seconds was used to avoid excessive pain. Each latency value was determined from two applications of the radiant heat stimulus, separated by 1–2 min intervals, and the mean of the two measures is taken. This test is similar to the hot plate test, except that repeated testing does not result in sensitization and the automatic endpoint minimizes the experimenter influence.

The injection of increasing doses of compound c (50–400 µg/kg, i.p.) did not affect plantar stimulation latencies in the Hargreaves test in control healthy mice.

Figure 5B:
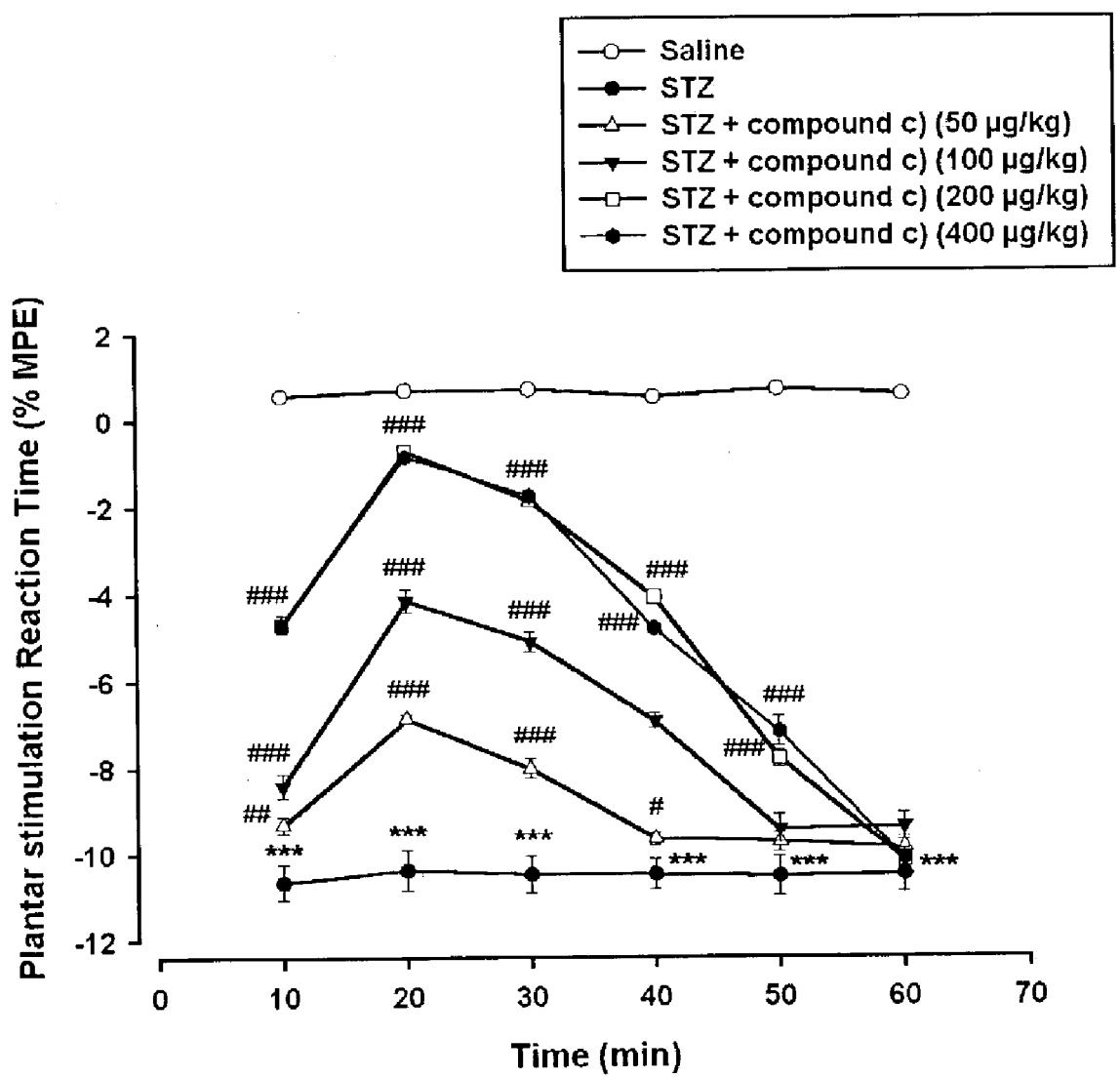

Acute i.p. administration of compound c as previously mentioned, produced a dose- and time-dependent inhibition of the hyperalgesic activity observed in diabetic mice in the same supra-spinal test (FIG. 5B). Its effect persisted for 50 min. The maximum effect was reached 20 min post the injection of all doses of compound c. The plantar stimulation reaction times in diabetic mice were significantly increased at the smaller doses (50 and 100 µg/kg) and latencies returned to basal values in control mice with the doses of 200 and 400 µg/kg. The MPE were $-6.87\pm0.11\%$, $-4.16\pm0.27\%$, $-0.71\pm0.06\%$ and $-0.85\pm0.08\%$ at 50, 100, 200 and 400 µg/kg, respectively, compared to $-10.38\pm0.46\%$ for the STZ diabetic mice (F=216.04, P<0.0001 (FIG. 5B). At 10, 30, 40 and 50 min following the administration of compound c, a comparable but weaker decrease in the hyperalgesic activity was obtained (F=87.71, P<0.0001, F=181.04, P<0.0001, F=156.04, P<0.0001, and F=16.48, P<0.0001 after 10, 30, 40 and 50 min, respectively), whereas the effect disappeared after 60 min (F=1.72, P>0.05) (FIG. 5B).

Figure 7B:
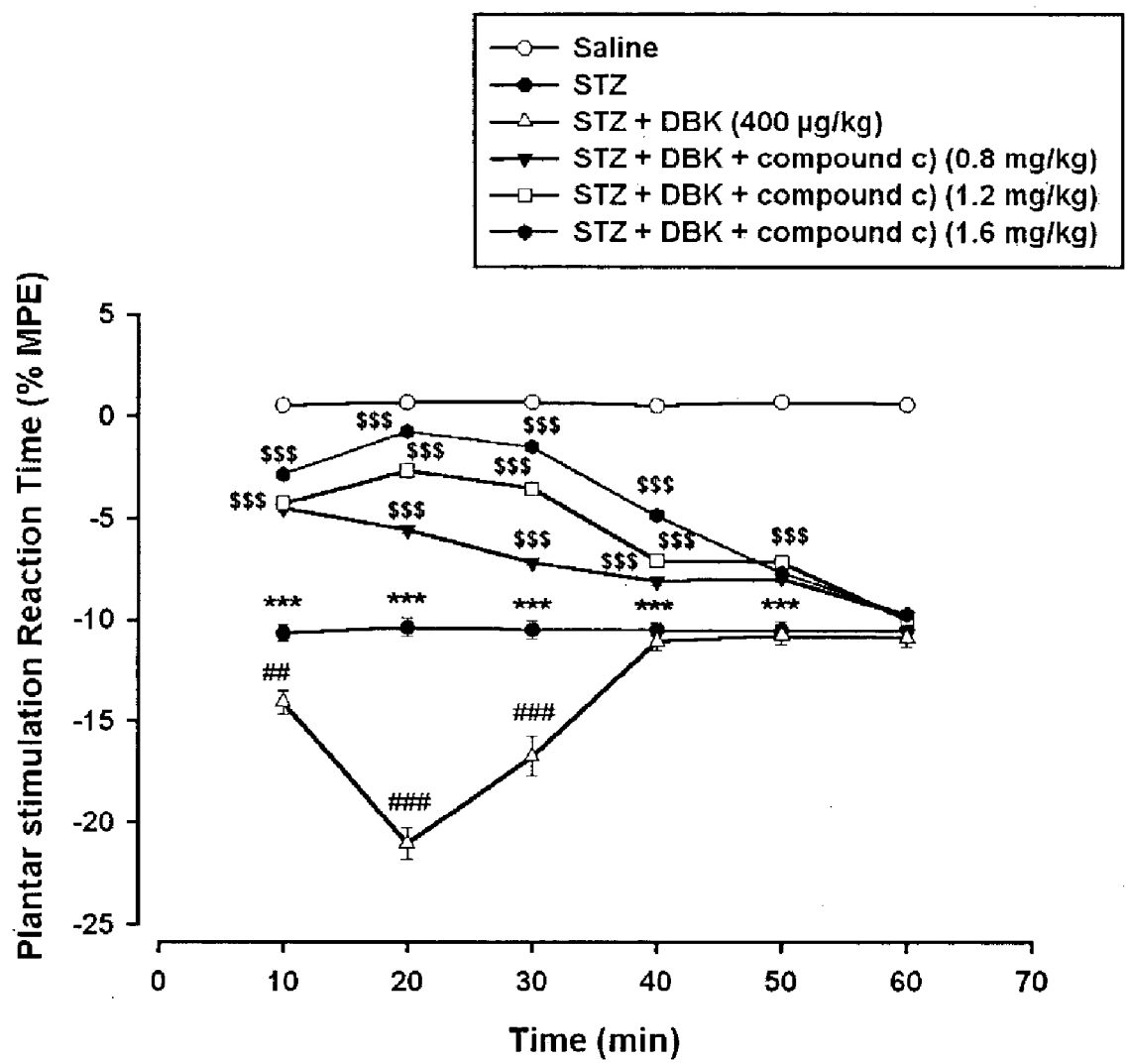

On the other hand, i.p. administration of the selective $BKB_1$ receptor agonist desArg$^9$BK (400 µg/kg), significantly potentiated the hyperalgesic response in STZ diabetic mice. The MPE measured 20 min following desArg$^9$BK injection, was reduced to $-21.03\pm0.75\%$ compared to $-10.38\pm0.46\%$ in control diabetic mice (FIG. 7B). It is noteworthy that treatment of healthy mice with desArg$^9$BK did not induce significant changes in nociceptive response in the plantar stimulation test.

Moreover, the co-administration of desArg$^9$BK with compound c, significantly and dose-dependently reversed the potentiating effect of desArg$^9$BK on STZ-induced hyperalgesia and produced a marked shift in the plantar stimulation latencies to values equivalent to those recorded in the control healthy mice. The MPE obtained at 20 min were to $-5.58\pm0.14\%$, $-2.67\pm0.17\%$ and $-0.75\pm0.04\%$ with 0.8, 1.2 and 1.6 mg/kg i.p. of compound c, respectively, versus $-21.03\pm0.75\%$ in the desArg$^9$BK-treated group (F=415.83, P<0.0001) (FIG. 7B).

In FIGS. 5A, 5B, 7A and 7B, diabetes was induced in CD-1 mice using streptozotocin (STZ; 200 mg/kg, i.p.). On day 7 following the induction of the disease, mice were injected with compound c (50–600 µg/kg, i.p.) and the hot plat and plantar stimulation tests were carried out at different time intervals (10, 20, 30, 40, 50 and 60 min) following compound c injection. Data are expressed as mean % MPE±SEM (n=8–12). MPE=Maximum Percent Effect; n=number of animals; *** significantly different from the saline group at P<0.001; #, ## and ### significantly different from the STZ group at P<0.05, P<0.01 and P<0.001, respectively; and $$ and $$$ significantly different from the STZ/desArg$^9$BK group at P<0.01 and P<0.001, respectively.

Tail Immersion Test

The tail-immersion test was performed according to Coderre and Rollman (Coderre and Rollman, 1983, Life Sci 32, 2139–2146). The mouse is gently wrapped in a towel, held at a 45° angle to a thermostatically controlled water bath set at 55±1° C. The latency between submersion of the tail and its removal from the water by the animal was recorded, with a maximum cut-off time of 10 seconds to minimize tail skin tissue damage. Mice with latency value between 2.5–4.0 seconds were selected.

Compound c, administered i.p. (<400 µg/kg) to control mice, showed no significant effect on nociception in the tail immersion test.

Figure 6A:
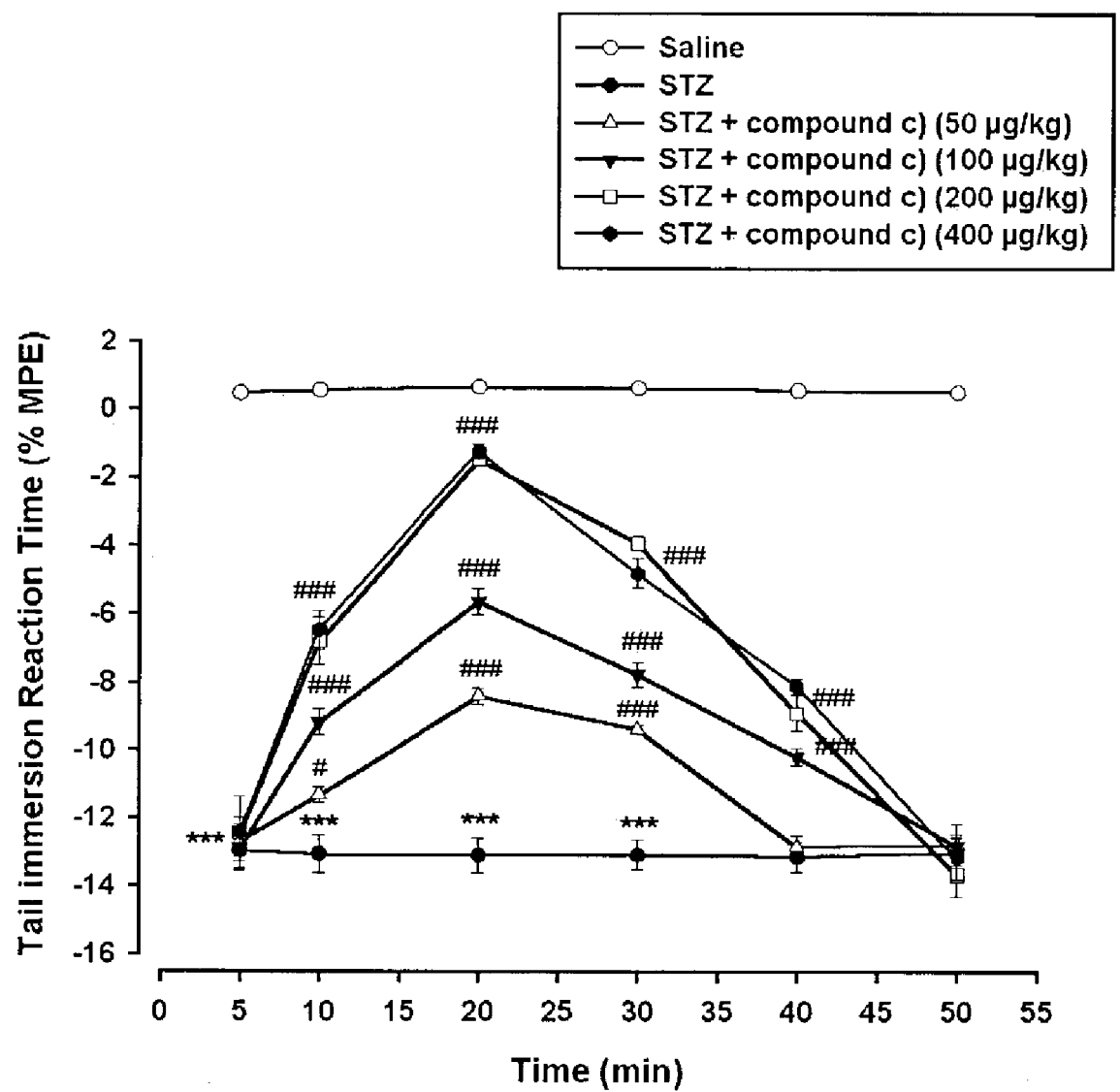
FIGS. 6A and 6B illustrate the effect of acute i.p. administration of the antagonist tested in FIGS. 2A and 2B on nociception in STZ diabetic mice in the tail immersion (FIG. 6A) and the tail flick (FIG. 6B) tests as spinal pain tests.

Compound c dose-dependently attenuated the hyperalgesic activity induced in diabetic mice. Its effect persisted for 40 min. The maximum effect for the compound c was reached 20 min following its injection. The reaction time of diabetic mice was significantly increased at relatively the smaller doses used (50 and 100 µg/kg) and the tail immersion latencies returned to basal values in control mice with the doses of 200, 400 µg/kg. The MPE were $-8.41\pm0.24\%$, $-5.65\pm0.38\%$, $-1.49\pm0.17\%$ and $-1.27\pm0.21$ with the doses of 50, 100, 200 and 400 µg/kg, respectively, compared to $-13.11\pm0.51\%$ for the STZ-treated mice (F=135.90, P<0.0001) (FIG. 6A). At 10, 30 and 40 min following the administration of compound c, a similar but weaker decrease in the hyperalgesic activity was obtained compared to that at 20 min (F=26.02, P<0.0001, F=86.54, P<0.0001 and F=26.74, P<0.0001 after 10, 30 and 40 min, respectively), whereas the analgesic effect disappeared after 50 min (F=0.27, P>0.5) (FIG. 6A).

Figure 8A:
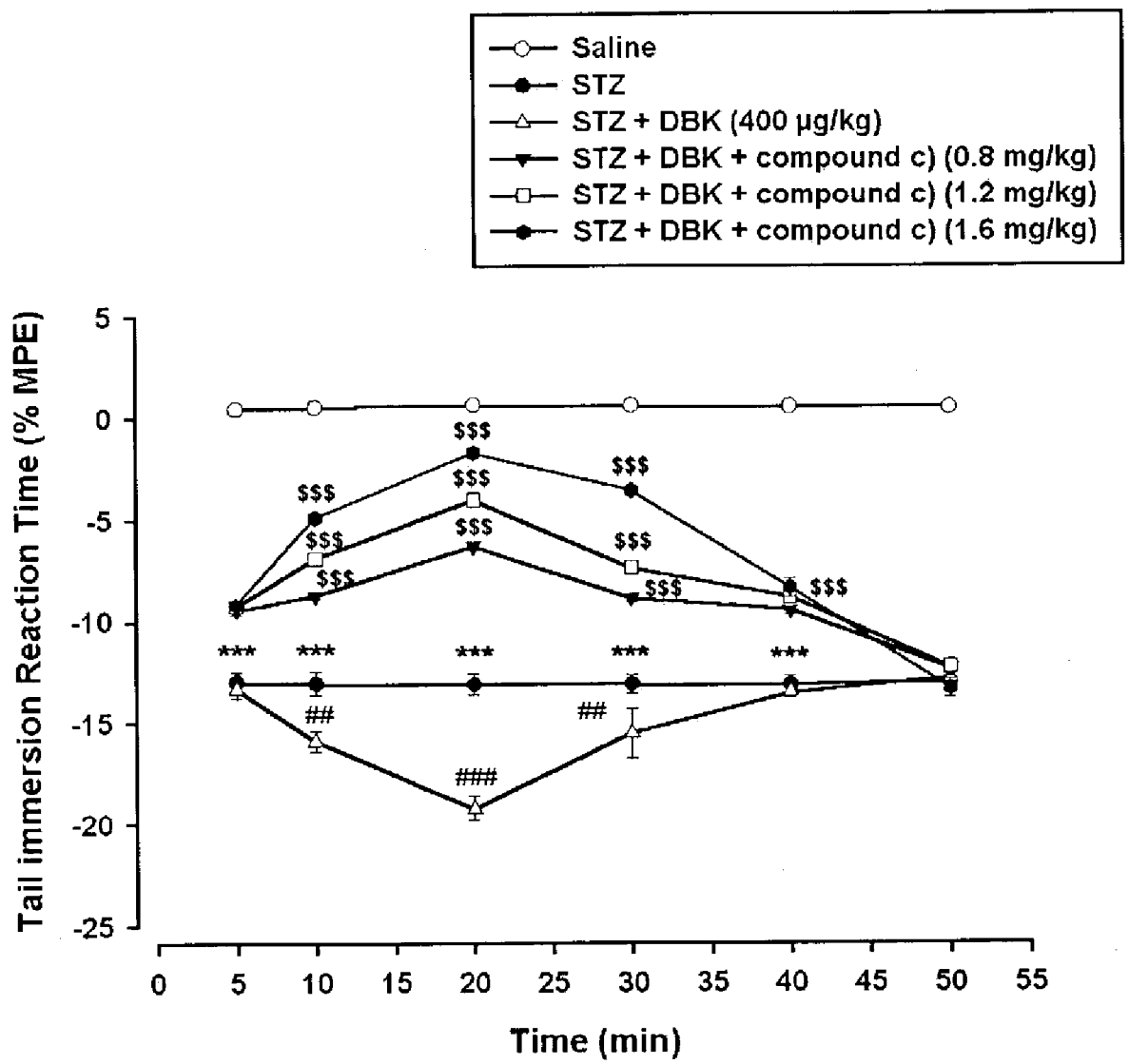
FIGS. 8A and 8B illustrate the effect of acute i.p. combined administration of desArg$^9$BK, a selective $BKB_1$ agonist with the antagonist tested in FIGS. 2A and 2B on nociception in STZ diabetic mice in the tail immersion (FIG. 8A) and the tail flick (FIG. 8B) tests.

Again in the tail immersion test, i.p. administration of the selective $BKB_1$ receptor agonist desArg$^9$BK, significantly potentiated the hyperalgesic response in STZ diabetic mice. The MPE obtained 20 min following the administration of desArg$^9$BK, decreased to $-19.23\pm0.60\%$ compared to $-13.11\pm0.51\%$ in control diabetic mice (FIG. 8A). Control mice treated with DBK did not show significant changes in the tail immersion latencies.

Further, compound c when co-administered with desArg$^9$BK, significantly and dose-dependently reversed the potentiating effect of desArg$^9$BK on STZ-induced hyperalgesia. Compound c increased the MPE in desArg$^9$BK-treated mice to $-6.33\pm0.18\%$, $-4.03\pm0.24\%$ and $-1.73\pm0.09\%$ with the doses of 0.8, 1.2 and 1.6 mg/kg of, respectively, compared to $-19.23\pm0.60\%$ in the desArg$^9$BK-treated group (F=132.30, P<0.001) (FIG. 8A).

Tail Flick Test

The tail flick test of D'Amour and Smith (D'Amour and Smith, 1941, J Pharmacol Exp Ther 72, 74–79) modified for mice was used. The mice are habituated in a plexiglass cylindrical mouse restrainer (4 cm in diameter and 8 cm long), 15 min daily for one week before starting the experiments. To measure the latency of the tail flick response, mice are gently placed in the restrainer and the tail put in the tail groove of the apparatus (Model IITC 336 Paw/Tail Stimulator Analgesia Meter, Life Science, Calif., USA). The tail-flick response is elicited by applying radiant heat from a halogen bulb lamp (150 W) to the dorsal surface of the animal tail. The radiant light is focussed on a blackened spot in the mid region of the animal's tail (2–3 cm from the tip of the tail) and the latency between the application of the stimulation light and the flicking of the animal's tail is recorded. When the animal flicks its tail, its exposes a photocell in the apparatus immediately below the tail and the instrument is automatically stopped and the time is recorded. A cut-off time of 10 sec is used to prevent blistering. The intensity of radiation is set to provide a pre-drug tail-flick response of 4–5 sec. This test is similar to the tail immersion test with the advantage that repeated testing does not result in sensitization and the automatic detection of the endpoint minimizes the experimenter influence.

Administration of increasing i.p. doses of compound c (<600 µg/kg) had no significant effect on nociception in the tail flick test in non-diabetic mice.

Figure 6B:
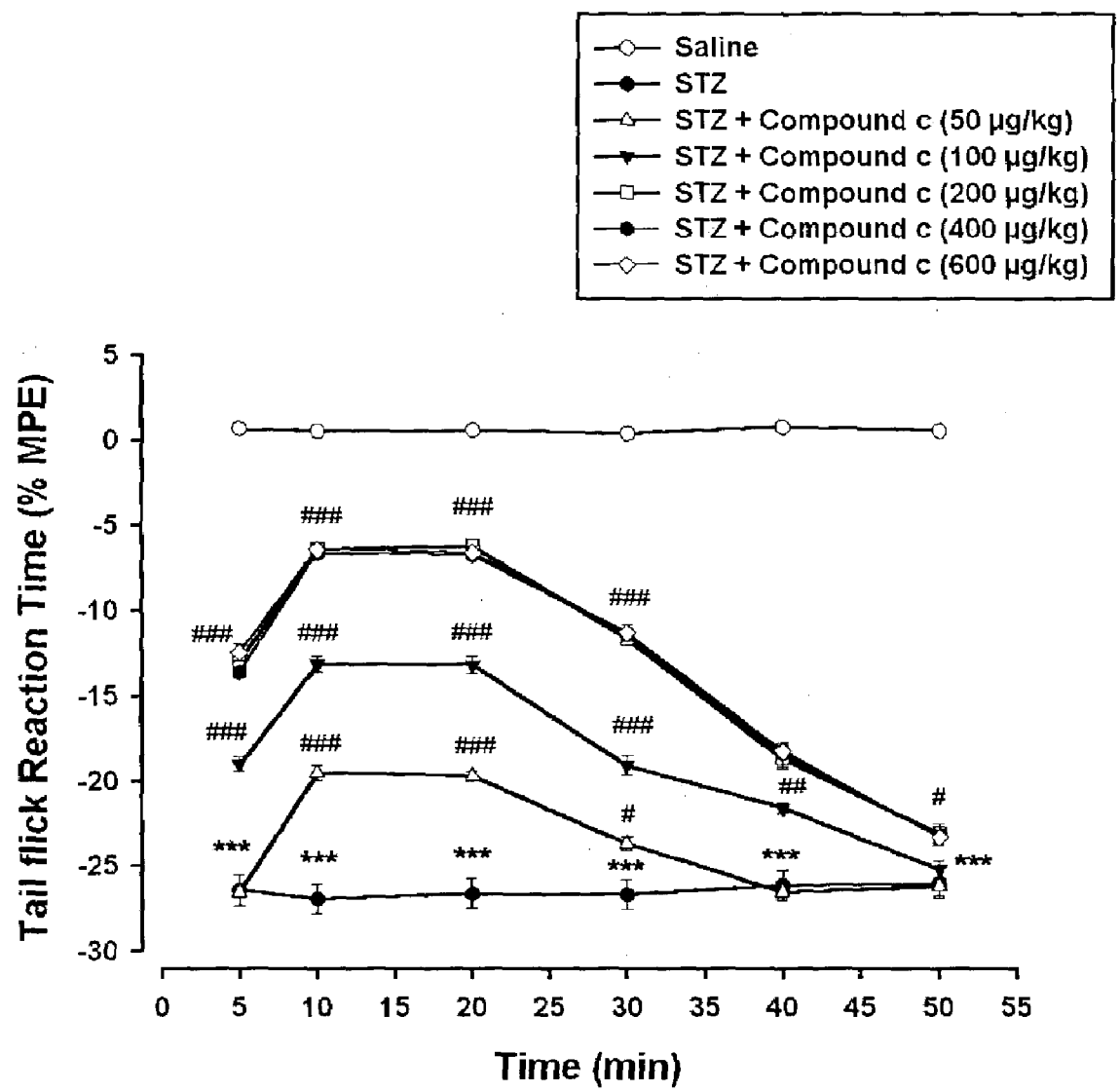

Conversely, it attenuated the hyperalgesic activity observed in diabetic mice in a dose- and time-dependent manner (FIG. 6B). Compound c (200 µg/kg and above) significantly inhibited by 76% (P<0.0001) the STZ-induced hyperalgesia after 10 min (FIG. 6B). Lower dosages (50, 100 µg/kg) still significantly (F=147.28, P<0.0001) inhibited the hyperalgesic activity by 28 and 51%, respectively, after 10 min. The inhibitory effect remained stable and receded after 20 min to ceased at 50 min (FIG. 6B). Compound c calculated $ID_{50}$ at the time of the maximal inhibition (10 min) was 72±2 µg/kg.

The i.p. administration of the $BKB_1$ receptor agonist desArg$^9$BK (400 µg/kg) to control mice did not induce significant changes in the tail flick test. Conversely, in STZ diabetic mice, desArg$^9$BK induced a marked increase in the hyperalgesic activity. The potentiating effect of desArg$^9$BK ( 48%) was maximal after 10 min (FIG. 8B).

Figure 8B:
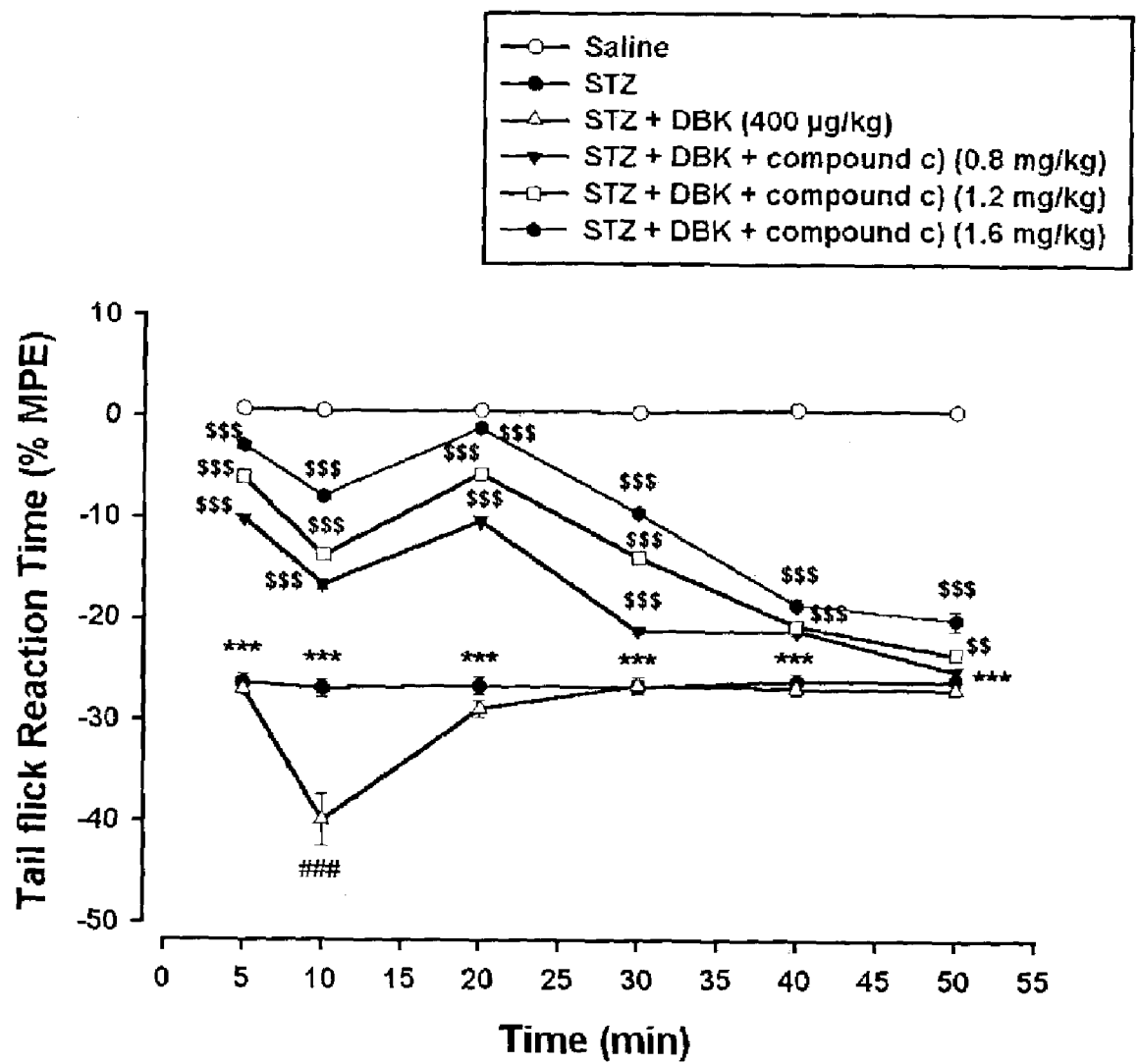

Co-administration of desArg$^9$BK and compound c in the tail flick test, exhibited similar profile to that shown in the other three tests in reversing the potentiating effect of desArg$^9$BK on diabetic hyperalgesia (FIG. 8B).

Results in FIGS. 6 and 8, are the means % MPE±SEM (n=7–12). MPE=Maximum Percent Effect; n=number of animals; *** significantly different from the saline group at P<0.001; #, ## and ### significantly different from the STZ group at P<0.05, P<0.01 and P<0.001, respectively; and $^{\$\$}$ and $^{\$\$\$}$ significantly different from the STZ/desArg$^9$BK group at P<0.01 and P<0.001, respectively.

The effect of the selected drugs on nociception was determined by converting the hot plate, the plantar stimulation, the tail immersion or the tail flick responses from latencies into MPE (Maximum Percent Effect) according to the following equation (Bhargava and Zhao, 1996, Neuropeptides, 30, 219–223):

$$(\% \, MPE) = \frac{(\text{Post-treatment latency} - \text{Pre-treatment latency})}{(\text{Cut-off time} - \text{Pre-treatment latency})} \times 100$$

In all tests, pre-treatment latencies were determined three times with an interval of 24 h starting three days before the injection of STZ or saline and the mean was calculated in order to obtain stable pre-drug response latency. On day seven following the injection of STZ, the selective $BKB_1$ receptor agonist desArg$^9$BK and/or the specific antagonists of the present invention were given i.p. and the effect of their acute administration on nociception were determined at different time intervals. The mice were divided into the following groups (n=6–10):
i) group control, treated with saline;
ii) group treated with STZ (200 mg/kg, i.p., once);
iii) group treated with STZ+compound c of the present invention as described above (50–600 µg/kg, i.p.);
iv) group treated with STZ+desArg$^9$BK (400 µg/kg, i.p.);
v) group treated with STZ+desArg$^9$BK+compound c of the present invention as described above (0.8–1.6 mg/kg, i.p.);
vi) group treated only with compound c of the present invention as described above; and
vii) group treated only with desArg$^9$BK.

In Vivo Assay of Vascular Permeability (Microcirculatory Leakage in Mice)

Male CD-1 mice weighing between 25–30 g (Charles River, St-Constant, QC, Canada) were used. All experiments were carried out in accordance with the ethical recommendations and guidelines of the Canadian Council on Animal Care. Mice were given a single i.p. dose of 200 mg/kg (McEvoy et al., 1994, supra) of STZ. Diabetes was confirmed by measuring blood glucose level, 96 h after STZ, using automatic analyzer. The diabetic animals used in the present study had a blood glucose level higher than 20 mmol/l.

Streptozotocin (Pharmacia & Upjohn Inc., Mississauga, ON, Canada) was dissolved in citrate buffer at a pH of 4.5 and administered i.p. to mice. Evans blue dye (EB; Sigma, St. Louis, Mo., USA) and compound c was dissolved in saline and administered i.v. to mice.

Conscious mice were given caudal venous injection of EB dye (20 mg/kg, in a final volume of 100 µl). The dye was allowed to circulate for 10 min and thereafter the mice were killed by cervical dislocation and exsanguinated (Béliveau et al., 2002, supra). The liver, pancreas, duodenum, ileum, spleen, heart, kidney, stomach, skin, muscle and thyroid were harvested, dissected and weighed, and a portion of each was immersed in formamide (4 ml/g wet weight at 24° C. for 24 h). The remaining portion was desiccated at 60° C. for 24 h. The concentration of EB dye extracted in formamide from selected tissues was determined spectrophotometrically at 620 nm using a Titertek Multiscan (Titertek, Instruments Inc., Huntsville, Ala., USA) against a standard curve and expressed as µg of EB per g of dry tissues.

Mice were divided into four groups of 4–6 animals: (i) control group, treated with saline; (ii) group treated with compound c (300 µg/kg, i.v.); (iii) group treated with STZ (200 mg/kg, i.p., once); (iv) group treated with STZ compound c described hereinabove. Four weeks after the induction of diabetes, the mice were given an acute i.v. injection of saline or compound c described hereinabove together with the EB dye and the vascular permeability test was performed 10 min later.

Figure 9:
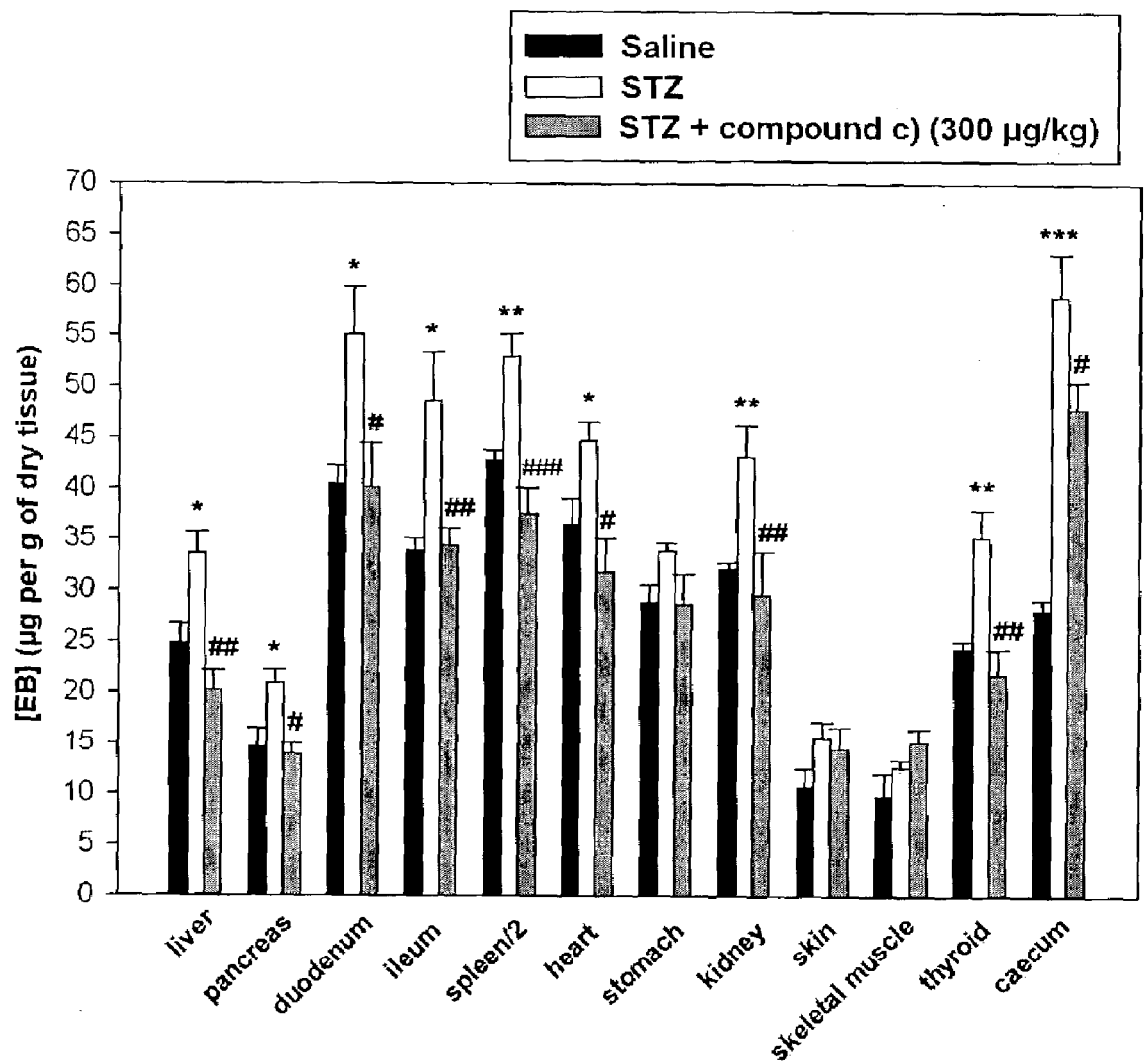
FIG. 9 illustrates the acute effect of the selective $BKB_1$ receptor antagonist tested in FIGS. 2A and 2B administered i.v. on vascular permeability changes associated with STZ-induced diabetes in mice.

STZ-induced diabetes was associated with marked alteration in vascular permeability, 4 weeks post-STZ injection in mice. As shown in FIG. 9, the capillary permeability to albumin-bound EB was increased, by 35% in the liver, 42% in the pancreas, 36% in the duodenum, 43% in the ileum, 24% in the spleen, 17% in the stomach, 22% in the heart, 34% in the kidney, 46% in the skin, 28% in the skeletal muscle, 46% in the thyroid gland and 110% in the caecum (P<0.001).

Acute i.v. administration of compound c (300 µg/kg, i.v.) to diabetic STZ diabetic mice at the same period of time, abolished the elevated vascular permeability in most tissues except the caecum where the plasma extravasation was reduced by 35% (P<0.001; FIG. 9). However, no significant changes in capillary permeability were observed in the skin or the skeletal muscle. It is noteworthy that treatment of control mice with compound c had no effect on the vascular permeability. These data provide further experimental evidence for the implication of $BKB_1$ receptor in the enhanced vascular permeability associated with type 1 diabetes. In FIG. 9, diabetes was induced in CD-1 mice using STZ (1×200 mg/kg, bolus i.p.). Four weeks following the induction of diabetes, animals were injected with saline or compound c (300 µg/kg, bolus i.v.), together with EB dye. Capillary permeability was assessed in selected tissues collected 10 min later, by quantifying the extravasation of albumin-bound EB. Data are expressed as mean [EB] (µg per g of dry tissue)±sem (n=4–6); n=number of animals; *, , * significantly different from the saline group at P<0.05, P<0.01 and P<0.001, respectively; # and ## significantly different from the STZ group at P<0.05 and P<0.01, respectively.

In vivo Assay of Inflammatory Allergic Asthma (in Mice)

Male Balb/c or C57B1/6 mice weighting 20–25 g (Charles River Laboratories, St-Constant, QC, Canada) were used. The mice were housed four by cage and maintained under conditions of standard lighting, (alternating 12-h light/dark cycle), temperature (22±0.5° C.) and humidity (60±10%) with food and water available at libitum.

Mice were sensitized on days 0 and 5 by intraperitoneal (i.p.) injections of 8 µg ovalbumin (OA) adsorbed to 2 mg aluminium hydroxide; $Al(OH)_3$ in saline (a total volume of 0.5 ml) according to the modified method of Kung et al. (Kung et al., 1994, Int Arch Allergy Immunol 105, 83–90). Control animals received equal volume of saline and Al $(OH)_3$. On days 12 and 13, animals were challenged for 30 min with 0.5% (w/v) OA solution (containing 0.8% antifoam B) in saline using an ultrasonic nebulizer (Model Spag-2, Montreal, PQ, Canada). Five min. before each of the two nebulizations, mice received intravenous (i.v.) injection of compound c or saline in the caudal vein in a volume of 100 µl. Animals were divided into the following groups: (i) sensitized group, treated with compound c (1, 10 and 100 µg/kg); (ii) control group which was given saline; and (iii) control group which was given compound c, respectively. Bronchoalveolar lavage (BAL) or airway hyperreactivity (AHR) measurements were performed 24 h after the second nebulization.

Bronchoalveolar cells were obtained from BAL of animals sacrificed following an i.m. injection of 50 µl of ketamine/xylazine (87/13 mg/kg). Briefly, the trachea was cannulated and the lungs were washed with 5 ml of PBS. The first 1 ml of bronchoalveolar lavage fluid (BALF) was collected and centrifuged (300×g, 10 min, 4° C.), and aliquots of the supernatant were removed and stored at −20 ° C. for albumin measurement. Total cell count was carried out using a hemocytometer, and viability was assessed with the Trypan blue exclusion test. Cell differential analysis was performed after cytocentrifugation and staining with Wright-Giemsa solution.

The involvement of the $BKB_1$ receptors in antigen-induced pulmonary inflammation was studied by evaluating the effect of compound c on inflammatory cells recruitment in the lungs of OA-sensitized Balb/c or C57B1/6 mice. The drug was injected i.v. or i.p., respectively, and cell migration was examined 24 h following the second OA challenge.

Figures 10A, 10B, 10C, 10D, 10E:
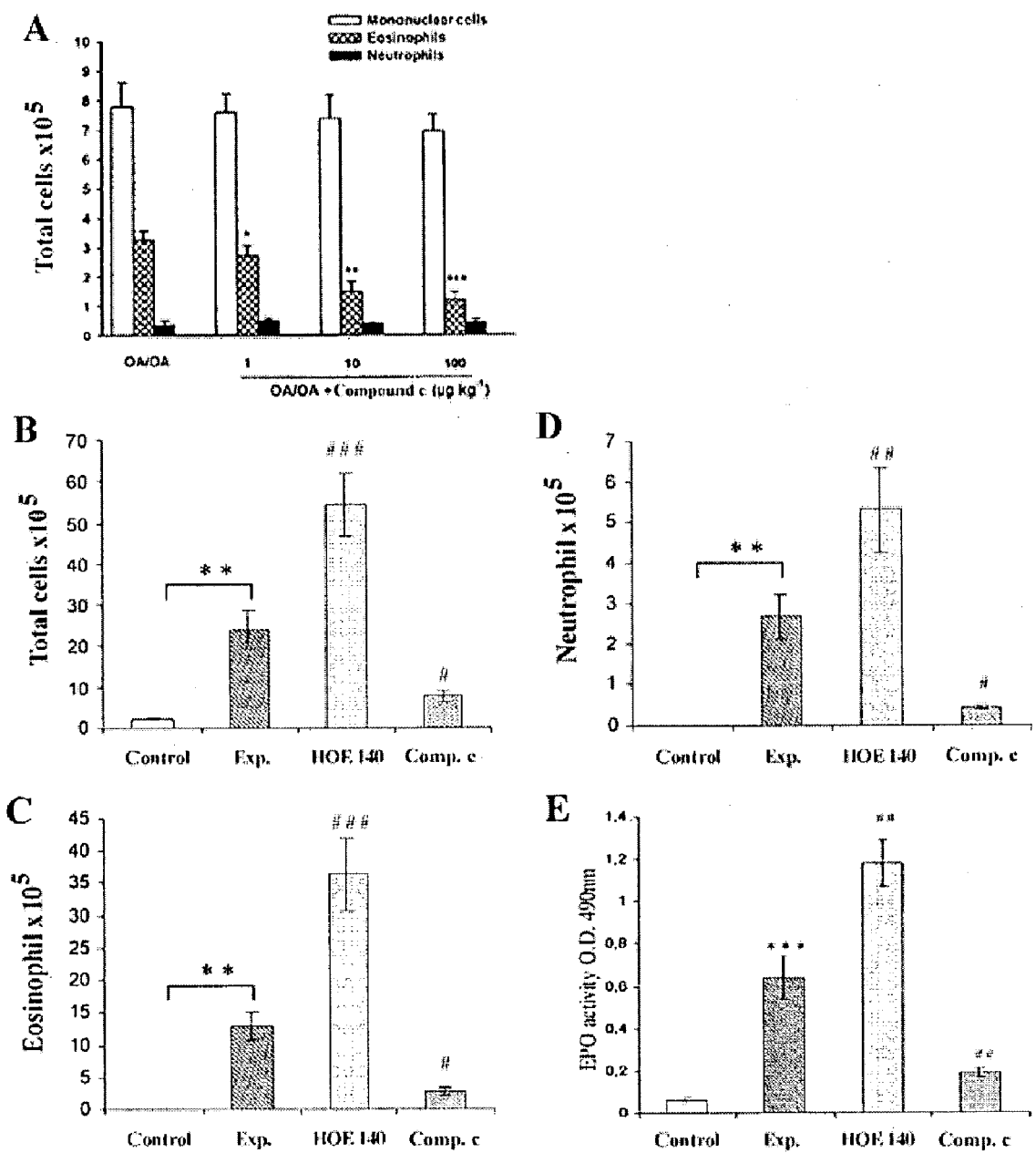
FIGS. 10A to 10E illustrate the effect of acute administration of the antagonist tested in FIGS. 2A and 2B on cell infiltration and $H_2O_2$ levels (eosinophil peroxydase) changes in the bronchoalveolar space associated with ovalbumin-challenged Balb/c (FIG. 10A) and C57BL/6 (FIGS. 10B to 10E) mice as models of allergic asthma.

The i.v. administration of compound c to Balb/c mice, five min before each OA-nebulization, produced a dose-dependent decrease in polymorphonuclears cells in bronchoalveolar space. Compound c decreased the OA-induced airway eosinophilia by 18% at a dose of 1 µg/kg (from $3.3\pm0.3\times10^5$ to $2.6\pm0.5\times10^5$ cells), by 54% at the dose of 10 µg/kg (from $3.3\pm0.3\times10^5$ to $1.5\pm0.3\times10^5$ cells) and by 64% at the dose of 100 µg/kg (from $3.3\pm0.3\times10^5$ to $1.2\pm0.4\times10^5$ cells) (P<0.001; FIG. 10A). In FIG. 10A, data are expressed as means ±SEM of 5–14 separate experiments. *,  and * denote values significantly different from OA/OA injected with saline at P<0.05, P<0.01 and P<0.001, respectively.

The i.p. administration of compound c (100 µg/kg) to C57B1/6 mice, 30 min before each antigen aerosol challenge, significantly reduced the total number of cells in BAL by 66.5% (from 24.532 to $8.214\times10^5$ cells) (P<0.001; FIG. 10B). Compound c also decreased the number of eosinophils from by 79.1% (from 12.911 to $2.708\times10^5$ cells) (P<0.001; FIG. 10C) and the number of neutrophils by 83.3% (from 2.675 to $0.45\times10^5$ cells), as measured in the BAL 24 h after the second challenge (P<0.001; FIG. 10D). The potent and stable antagonist also inhibited by 75.31% the eosinophil peroxidase activity measured in BAL cell suspensions (FIG. 10E). Results in FIG. 10B–E are the mean ±SEM of 7–8 animal groups. Values significantly different from control at ** P<0.01 and P<0.001, respectively and values significantly different from experimental group at # P<0.01 and ##P<0.001, respectively.

These results show that activation of $BKB_1$ receptor is involved in the airway inflammatory response induced by antigen challenge in mice.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of the formula (I)

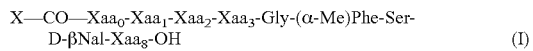
                                                            (I)

wherein

X is $C_nH_{2n}+1$ or $C_iH_{2i}-C_6H_5$, where n is an integer from 1 to 3 and i is an integer from 0 to 3

$Xaa_0$ is Orn or Cit;

$Xaa_1$ is Arg or Cit;

$Xaa_2$ is Oic, Hyp or Pro;

$Xaa_3$ is Pro or Oic; and $Xaa_8$ is Ile, Leu or Nle.

2. The compound of claim 1, wherein $Xaa_1$ is Arg and $Xaa_8$ is Ile.

3. The compound of claim 1, wherein $Xaa_2$ is Oic and $Xaa_3$ is Pro.

4. A compound selected from the group consisting of:

Ac-Orn[Oic$^2$,($\alpha$-Me)Phe$^5$,D-$\beta$Nal$^7$,Ile$^8$]desArg$^9$BK;
Ac-Lys[Oic$^2$,($\alpha$-Me)Phe$^5$,D-$\beta$Nal$^7$,Ile$^8$]desArg$^9$BK;
Ac-Orn[Oic$^2$,Oic$^3$($\alpha$-Me)Phe$^5$,D-$\beta$Nal$^7$,Ile$^8$]desArg$^9$BK;
Ac-Lys[Oic$^2$,Oic$^3$($\alpha$-Me)Phe$^5$,D-$\beta$Nal$^7$,Ile$^8$]desArg$^9$BK;
Propanoyl-Orn[Oic$^2$,($\alpha$-Me)Phe$^5$,D-$\beta$Nal$^7$,Ile$^8$] desArg$^9$BK;
Propanoyl-Lys[Oic$^2$,($\alpha$-Me)Phe$^5$,D-$\beta$Nal$^7$,Ile$^8$] desArg$^9$BK;
Propanoyl-Orn[Oic$^2$,Oic$^3$($\alpha$-Me)Phe$^5$,D-$\beta$Nal$^7$,Ile$^8$] desArg$^9$BK;
Propanoyl-Lys[Oic$^2$,Oic$^3$($\alpha$-Me)Phe$^5$,D-$\beta$Nal$^7$,Ile$^8$] desArg$^9$BK;
Butanoyl-Orn[Oic$^2$,($\alpha$-Me)Phe$^5$,D-$\beta$Nal$^7$,Ile$^8$] desArg$^9$BK
Butanoyl-Lys[Oic$^2$,($\alpha$-Me)Phe$^5$,D-$\beta$Nal$^7$,Ile$^8$] desArg$^9$BK;
Butanoyl-Orn[Oic$^2$,Oic$^3$($\alpha$-Me)Phe$^5$,D-$\beta$Nal$^7$,Ile$^8$] desArg$^9$BK;
Butanoyl-Lys[Oic$^2$,Oic$^3$($\alpha$-Me)Phe$^5$,D-$\beta$Nal$^7$,Ile$^8$] desArg$^9$BK;
Bz-Orn[Oic$^2$,($\alpha$-Me)Phe$^5$,D-$\beta$Nal$^7$,Ile$^8$]desArg$^9$BK;
Bz-Lys[Oic$^2$,($\alpha$-Me)Phe$^5$,D-$\beta$Nal$^7$,Ile$^8$]desArg$^9$BK;
Bz-Orn[Oic$^2$,Oic$^3$($\alpha$-Me)Phe$^5$,D-$\beta$Nal$^7$,Ile$^8$]desArg$^9$BK;
Bz-Lys[Oic$^2$,Oic$^3$($\alpha$-Me)Phe$^5$,D-$\beta$Nal$^7$,Ile$^8$]desArg$^9$BK;
2-phenyl-acetyl-Orn[Oic$^2$,($\alpha$-Me)Phe$^5$,D-$\beta$Nal$^7$,Ile$^8$] desArg$^9$BK;
2-phenyl-acetyl-Lys[Oic$^2$,($\alpha$-Me)Phe$^5$,D-$\beta$Nal$^7$,Ile$^8$] desArg$^9$BK;
2-phenyl-acetyl-Orn[Oic$^2$,Oic$^3$($\alpha$-Me)Phe$^5$,D-$\beta$Nal$^7$,Ile$^8$] desArg$^9$BK;
2-phenyl-acetyl-Lys[Oic$^2$,Oic$^3$($\alpha$-Me)Phe$^5$,D-$\beta$Nal$^7$,Ile$^8$] desArg$^9$BK;
3-phenyl-propanoyl-Orn[Oic$^2$,($\alpha$-Me)Phe$^5$,D-$\beta$Nal$^7$,Ile$^8$] desArg$^9$BK;
3-phenyl-propanoyl-Lys[Oic$^2$,($\alpha$-Me)Phe$^5$,D-$\beta$Nal$^7$,Ile$^8$] desArg$^9$BK;
3-phenyl-propanoyl-Orn[Oic$^2$,Oic$^3$($\alpha$-Me)Phe$^5$,D-$\beta$Nal$^7$, Ile$^8$]desArg$^9$BK;
3-phenyl-propanoyl-Lys[Oic$^2$,Oic$^3$($\alpha$-Me)Phe$^5$,D-$\beta$Nal$^7$, Ile$^8$]desArg$^9$BK;
4-phenyl-butanoyl-Orn[Oic$^2$,($\alpha$-Me)Phe$^5$,D-$\beta$Nal$^7$,Ile$^8$] desArg$^9$BK;
4-phenyl-butanoyl-Lys[Oic$^2$,($\alpha$-Me)Phe$^5$,D-$\beta$Nal$^7$,Ile$^8$] desArg$^9$BK;
4-phenyl-butanoyl-Orn[Oic$^2$,Oic$^3$($\alpha$-Me)Phe$^5$,D-$\beta$Nal$^7$, Ile$^8$]desArg$^9$BK; and
4-phenyl-butanoyl-Lys[Oic$^2$,Oic$^3$($\alpha$-Me)Phe$^5$,D-$\beta$Nal$^7$, Ile$^8$]desArg$^9$BK.

5. The compound Ac-Orn[Oic$^2$,($\alpha$-Me)Phe$^5$,D-$\beta$Nal$^7$, Ile$^8$]desArg$^9$BK.

6. A pharmaceutical composition comprising a therapeutically effective amount of a compound as defined in claim 1 and a pharmaceutically acceptable carrier.

7. A method for treating inflammation, pain and diabetic lesions, said method comprising the step of administering to a patient in need thereof a compound as defined in claim 1.

8. A method for treating airway and lung inflammation, said method comprising the step of administering to a patient in need thereof a compound as defined in claim 1.

9. A method for treating asthma comprising the step of administering to a patient in need thereof a compound as defined in claim 1.

10. A method for treating inflammation comprising the step of administering to a patient in need thereof a compound as defined in claim 1.

11. A method for treating pain and hyperlagesia comprising the step of administering to a patient in need thereof a compound as defined in claim 1.

12. A method for treating microcirculatory dysfunction comprising the step of administering to a patient in need thereof a compound as defined in claim 1.

13. A method for treating cellular infiltration and activation into bronchoalveolar space comprising the step of administering to a patient in need thereof a compound as defined in claim 1.

14. A method for treating inflammation, pain, hyperalgesia and vasculopaties in diabetes comprising the step of administering to a patient in need thereof a compound as defined in claim 1.

15. A method for treating inflammation, cell infiltration an activation in asthma comprising the step of administering to a patient in need thereof a compound as defined in claim 1.

* * * * *

UNITED STATES PATENT AND TRADEMARK OFFICE
CERTIFICATE OF CORRECTION

PATENT NO. : 7,211,566 B2
APPLICATION NO. : 10/405088
DATED : May 1, 2007
INVENTOR(S) : Regoli et al.

It is certified that error appears in the above-identified patent and that said Letters Patent is hereby corrected as shown below:

On title page, item 75 Inventors, replace

"Domenico Regoli, Magog (CA);
Witold Neugebauer, Ottawa (CA);
Fernand Gobeil, Sherbrooke (CA);
Bichov Gabra, Fleurimont (CA);
Pierre Sirois, Orford (CA)" with -- Domenico Regoli, Magog (CA);
Witold A. Neugebauer, Ottawa (CA);
Fernand Gobeil, Sherbrooke (CA);
Bichoy Gabra, Fleurimont (CA);
Pierre Sirois, Orford (CA) --.

Signed and Sealed this

Nineteenth Day of June, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Bradykinin

<400> SEQUENCE: 1

Arg Pro Pro Gly Phe Ser Pro Phe Arg
1               5

<210> SEQ ID NO 2
<211> LENGTH: 10
<212> TYPE: PRT

```
<213> ORGANISM: Artificial Sequence
<220> FEATURE:
<223> OTHER INFORMATION: Lys-Bradykinin

<400> SEQUENCE: 2

Lys Arg Pro Pro Gly Phe Ser Pro Phe Arg
 1               5                  10

<210> SEQ ID NO 3
<211> LENGTH: 8
<212> TYPE: PRT
<213> ORGANISM: Artificial Sequence
<220> FEATURE:
<223> OTHER INFORMATION: des-Arg9 Bradykinin

<400> SEQUENCE: 3

Arg Pro Pro Gly Phe Ser Pro Phe
 1               5

<210> SEQ ID NO 4
<211> LENGTH: 9
<212> TYPE: PRT
<213> ORGANISM: Artificial Sequence
<220> FEATURE:
<223> OTHER INFORMATION: Lys - des-Arg9 Bradykinin

<400> SEQUENCE: 4

Lys Arg Pro Pro Gly Phe Ser Pro Phe
 1               5
```